United States Patent
Wong et al.

(10) Patent No.: US 10,709,119 B2
(45) Date of Patent: Jul. 14, 2020

(54) METHODS OF AGENT DELIVERY INTO EGGS AND EMBRYOS OF EGG-PRODUCING AQUATIC ANIMALS FOR DRUG SCREENING, AGENT TOXICITY ASSAY AND PRODUCTION OF INFERTILE FISH

(71) Applicant: University of Maryland Baltimore County, Baltimore, MD (US)

(72) Inventors: Ten-Tsao Wong, Timonium, MD (US); Yonathan Zohar, Baltimore, MD (US)

(73) Assignee: UNIVERSITY OF MARYLAND BALTIMORE COUNTY, Baltimore, MD (US)

( * ) Notice: Subject to any disclaimer, the term of this patent is extended or adjusted under 35 U.S.C. 154(b) by 155 days.

(21) Appl. No.: 15/568,729

(22) PCT Filed: May 17, 2016

(86) PCT No.: PCT/US2016/032873
§ 371 (c)(1),
(2) Date: Oct. 23, 2017

(87) PCT Pub. No.: WO2016/187198
PCT Pub. Date: Nov. 24, 2016

(65) Prior Publication Data
US 2018/0295817 A1    Oct. 18, 2018

Related U.S. Application Data

(60) Provisional application No. 62/163,511, filed on May 19, 2015, provisional application No. 62/274,958, filed on Jan. 5, 2016.

(51) Int. Cl.
| | | |
|---|---|---|
| *C12N 15/113* | (2010.01) | |
| *C12N 15/87* | (2006.01) | |
| *A01K 67/027* | (2006.01) | |
| *C12Q 1/68* | (2018.01) | |

(52) U.S. Cl.
CPC ........ *A01K 67/0275* (2013.01); *A01K 67/027* (2013.01); *C12N 15/113* (2013.01); *C12N 15/87* (2013.01); *A01K 2207/05* (2013.01); *A01K 2207/20* (2013.01); *A01K 2227/40* (2013.01); *A01K 2267/02* (2013.01); *A01K 2267/03* (2013.01); *C12N 2310/11* (2013.01); *C12N 2310/3233* (2013.01); *C12N 2310/351* (2013.01); *C12N 2320/32* (2013.01); *Y02A 90/40* (2018.01)

(58) Field of Classification Search
None
See application file for complete search history.

(56) References Cited

U.S. PATENT DOCUMENTS

| | | | |
|---|---|---|---|
| 7,194,978 B2 | 3/2007 | Zohar et al. | |
| 7,935,816 B2 | 5/2011 | Li | |
| 9,999,208 B2 * | 6/2018 | Zohar | .......... C12N 15/113 |
| 10,136,621 B2 * | 11/2018 | Zohar | .......... C12N 15/113 |
| 2005/0132969 A1 | 6/2005 | Zohar et al. | |
| 2010/0212039 A1 | 8/2010 | Wu et al. | |
| 2014/0261212 A1 | 9/2014 | Peterson et al. | |
| 2016/0286768 A1 | 10/2016 | Zohar et al. | |
| 2018/0288984 A1 * | 10/2018 | Zohar | .......... C12N 15/113 |

FOREIGN PATENT DOCUMENTS

| | | |
|---|---|---|
| CN | 1528131 A | 8/2004 |
| CN | 1528131 A | 9/2004 |
| CN | 1559201 | 1/2005 |
| CN | 1559201 A | 1/2005 |
| CN | 101652475 A | 2/2010 |
| EP | 2535404 A1 | 12/2012 |
| WO | 2005001028 A1 | 1/2005 |
| WO | 2009055027 A2 | 4/2009 |
| WO | WO2011099528 A1 | 8/2011 |

(Continued)

OTHER PUBLICATIONS

Wessel, G., et al., "Cell Surface Changes in the Egg at Fertilization", "Mol Reprod Dev", 2009, pp. 942-953, vol. 76, No. 10.
Wada, T., et al., "Antisense Morpholino Targeting Just Upstream From a Poly(A) Tail Junction of Maternal mRNA Removes the Tail and Inhibits Translation", "Nucleic Acids Research", 2012, p. 1-10, vol. 40, No. 22.
Yuan, S., et al., "Microinjection of mRNA and Morpholino Antisense Oligonucleotides in Zebrafish Embryos", "Journal of Visualized Experiments", 2009, pp. 1-3, vol. 27, No. e1113.
Beloor, J., et al., "Arginine-Engrafted Biodegradable Polymer for the Systemic Delivery of Therapeutic siRNA", "Biomaterials", 2012, pp. 1640-1650, vol. 33.

(Continued)

*Primary Examiner* — Sean McGarry
(74) *Attorney, Agent, or Firm* — Hultquist, PLLC; Steven J. Hultquist

(57) ABSTRACT

Methods are provided for delivery of at least one agent into egg(s) from an egg-producing aquatic animal including contacting fertilized or unfertilized egg(s) from said egg-producing aquatic animal with the at least one agent in the presence of a guanidine-containing compound capable of enhancing the permeability of the chorion of the egg(s). Methods are provided for the drug screening and compound toxicity assays. Methods are also provided for the production of reproductively sterile fish and aquatic animals for aquaculture, the aquarium trade, and control of invasive species are described. The methods include disruption of gonadal development through the administration of agents that lead to the failure of fertile gonadal development. Agents may be delivered to the eggs directly before the fertilization or post fertilization by contacting eggs in an immersion medium including the agent of interest.

33 Claims, 9 Drawing Sheets
(8 of 9 Drawing Sheet(s) Filed in Color)

Specification includes a Sequence Listing.

(56) References Cited

FOREIGN PATENT DOCUMENTS

| WO | 2012106026 A2 | 8/2012 |
|---|---|---|
| WO | 2013054123 A1 | 4/2013 |
| WO | 2015073819 A1 | 5/2015 |

OTHER PUBLICATIONS

Kim, T., et al., "Arginine-Grafted Bioreducible Poly(disulfide amine) for Gene Delivery Systems", "Biomaterials", 2009, pp. 658-664, vol. 30.

Wu, R., et al., "Cell-Penetrating Peptides as Transporters for Morpholino Oligomers: Effects of Amino Acid Composition on Intracellular Delivery and Cytotoxicity", "Nucleic Acids Research", 2007, pp. 5182-5191, vol. 35, No. 15.

Abraham, E., et al., "Targeted Gonadotropin-Releasing Hormone-3 Neuron Ablation in Zebrafish: Effects on Neurogenesis, Neuronal Migration, and Reproduction", "Endocrinology", Oct. 27, 2009, pp. 332-340, vol. 151.

Chen, C., et al., "Chorion microstructure for identifying five fish eggs of Apogonidae", "Journal of Fish Biology", Aug. 21, 2007, pp. 913-919, vol. 71.

Ciruna, B., et al., "Production of maternal-zygotic mutant zebrafish by germ-line replacement", "PNAS", Nov. 12, 2002, pp. 14919-14924, vol. 99, No. 23.

Cotelli, F., et al., "Structure and Composition of the Fish Egg Chorion (*Carassius auratus*)", "Journal of Ultrastructure and Molecular Structure Research", Apr. 1988, pp. 70-78, vol. 99.

Fujimoto, T., et al., "Sexual dimorphism of gonadal structure and gene expression in germ cell-deficient loach, a teleost fish", "PNAS", Oct. 5, 2010, pp. 17211-17216, vol. 107, No. 40.

Gellert, G., et al., "Effect of age on the susceptibility of zebrafish eggs to industrial wastewater.", "Water Res.", Oct. 2001, pp. 3754-3757, vol. 35, No. 15.

Hagedorn, M., et al., "Water Distribution and Permeability of Zebrafish Embryos, *Brachydanio rerio*", "The Journal of Experimental Zoology", 1997, pp. 356-371, vol. 278.

Hu, W., et al, "Antisense for gonadotropin-releasing hormone reduces gonadotropin synthesis and gonadal development in transgenic common carp (*Cyprinus carpio*)", "Aquaculture", 2007, pp. 498-506, vol. 271.

Kais, B. et al., "DMSO Modifies the Permeability of the Zebrafish (*Danio rerio*) chorion—Implications for the Fish Embryo Test (FET)", "Aquatic Toxicology", May 28, 2013, pp. 229-238, vol. 140-141.

Li, Y., et al., "Design and Synthesis of Dendritic Molecular Transporter that Achieves Efficient in Vivo Delivery of Morpholino Antisense Oligo", "Bioconjugate Chemistry", Jun. 20, 2008, pp. 1464-1470, vol. 19, No. 7.

Linfiartova, Z., et al., "Sterilization of sterlet Acipenser ruthenus by using knockdown agent, antisense morpholino oligonucleotide, against dead end gene", "Theriogenology", 2015, pp. 1246-1255, vol. 84.

Morcos, P., et al., "Vivo-Morpholinos: A non-peptide transporter delivers Morpholinos into a wide array of mouse issues", "BioTechniques", Dec. 2008, pp. 613-623, vol. 45.

Pantos, A., et al., "Guanidinium Group: A Versatile Moiety Inducing Transport and Multicompartmentalization in Complementary Membranes", "Biochimica et Biophysica Acta", Dec. 12, 2007, pp. 811-823, vol. 1778.

Skugor, A., et al., "Knockdown of the Germ Cell Factor Dead End Induces Multiple Transcriptional Changes in Atlantic Cod (*Gadus morhua*) Hatchlings", "Animal Reproductive Science", Dec. 31, 2013, pp. 129-137, vol. 144.

Slanchev, K., et al., "Development without germ cells: The role of the germ line in zebrafish sex differentiation", "PNAS", Mar. 15, 2005, pp. 4074-4079, vol. 102, No. 11.

Slanchev, K., et al., "Control of dead end localization and activity implications for the function of the protein in antagonizing mlRNA function", "Mechanisms of Development", Oct. 25, 2008, pp. 270-277, vol. 126.

Terner, C., "Studies of Metagolism in Embronic Development—I. The Oxidative Metabolism of Unfertilized and Embryonated Eggs of the Rainbow Trout", "Comp. Biochem. Physiol.", Mar. 1968, pp. 933-940, vol. 24.

Theodossiou, T.A., et al., "Guanidinylated Dendritic Molecular Transporters: Prospective Drug Delivery Systems and Application in Cell Transfection", "ChemMedChem", Nov. 4, 2008, pp. 1635-1643, vol. 3.

Weidinger, G., et al., "dead end, a Novel Vertebrate Germ Plasm Component, Is Required for Zebrafish Primordial Germ Cell Migration and Survival", "Current Biology", Aug. 19, 2003, pp. 1429-1434, vol. 13.

Wender, P., et al., "The Design of Guanidinium-Rich Transporters and Their Internalization Mechanisms", "Advanced Drug Delivery Reviews", Dec. 31, 2007, pp. 452-472, vol. 60.

Wong, T.T., et al., "Production of Reproductively Sterile Fish by a Non-Transgenic Gene Silencing Technology", "Scientific Reports", Oct. 29, 2015, vol. 5, No. 15822.

Wong, T.T., et al, "Production of Reproductively Sterile Fish: a Mini-Review of Germ Cell Elimination Technologies", "General and Comparitive Endrocrinology", Jan. 9, 2015, pp. 3-8, vol. 221.

Wong, T., et al, "Inducible Sterilization of Zebrafish by Disruption of Primordial Germ Cell Migration", "PLOS ONE", Jun. 2013, p. e68455 (1-8), vol. 8, No. 6.

Xu, Jing, et al., "Defining Global Gene Expression Changes of the Hypothalamic-Pituitary-Gonadal Axis in Female sGnRHAntisense Transgenic Common Carp (*Cyprinus carpio*)", "PLoS One", Jun. 2011, p. e 21057 (12 pages), vol. 6, No. 6.

Note: For the non-patent literature citations that no month of publication is indicated, the year of publication is more than 1 year prior to the effective filing date of the present application.

Alhakamy, N., et al., "Polyarginine Molecular Weight Determines Transfection Efficiency of Calcium Condensed Complexes", "Molecular Pharmaceutics", 2013, pp. 1940-1948, vol. 10, No. 5.

* cited by examiner

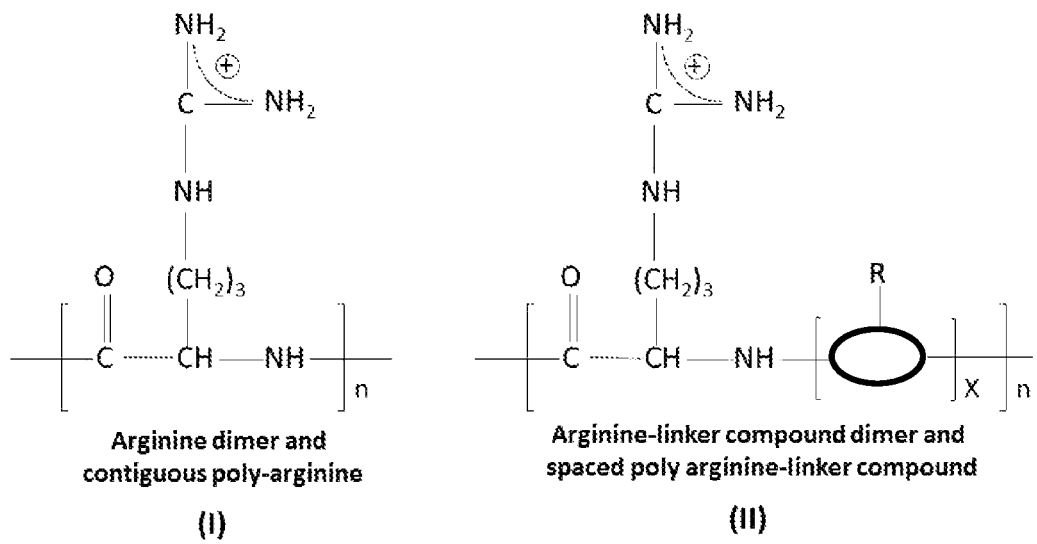

Arginine dimer and
contiguous poly-arginine (I)

Arginine-linker compound dimer and
spaced poly arginine-linker compound (II)

R: Variable group   ◯: Variable backbone linker   n ≥ 2; x ≥ 1

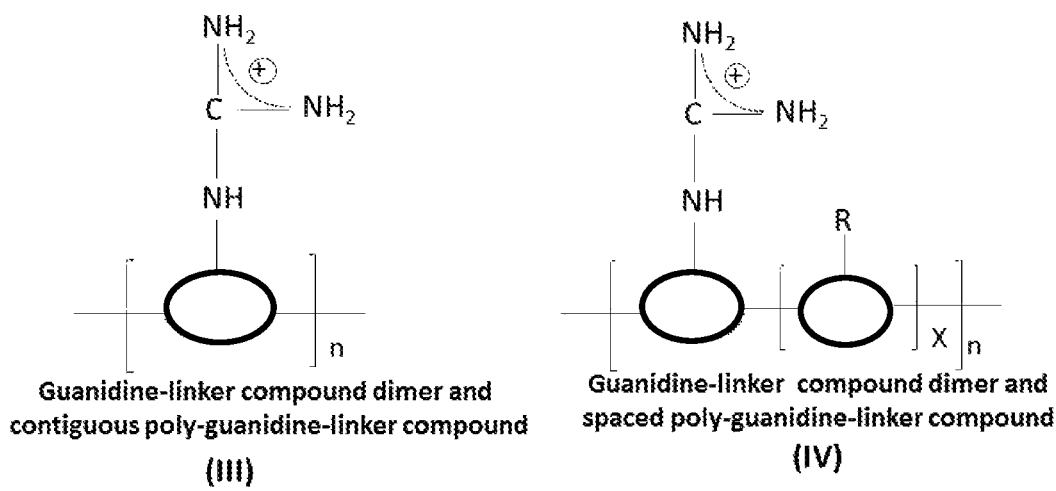

Guanidine-linker compound dimer and
contiguous poly-guanidine-linker compound (III)

Guanidine-linker compound dimer and
spaced poly-guanidine-linker compound (IV)

R: Variable group   ◯: Variable backbone linker   n ≥ 2; x ≥ 1

FIG. 9

SEQUENCE LISTING

```
<160> NUMBER OF SEQ ID NOS: 3

<210> SEQ ID NO 1
<211> LENGTH: 12
<212> TYPE: DNA
<213> ORGANISM: Salmo salar

<400> SEQUENCE: 1
acgctcctcc at                                                         12

<210> SEQ ID NO 2
<211> LENGTH: 18
<212> TYPE: DNA
<213> ORGANISM: Salmo salar

<400> SEQUENCE: 2
acttgaacgc tcctccat                                                   18
```

```
<210> SEQ ID NO 3
<211> LENGTH: 25
<212> TYPE: DNA
<213> ORGANISM: Salmo salar

<400> SEQUENCE: 3
ctgacttgaa cgctcctcca ttatc                                           25
```

METHODS OF AGENT DELIVERY INTO EGGS AND EMBRYOS OF EGG-PRODUCING AQUATIC ANIMALS FOR DRUG SCREENING, AGENT TOXICITY ASSAY AND PRODUCTION OF INFERTILE FISH

CROSS-REFERENCE TO RELATED APPLICATIONS

This application is a U.S. national phase under the provisions of 35 U.S.C. § 371 of International Patent Application No. PCT/US2016/032873 filed May 17, 2016, which in turn claims benefit of priority of U.S. Provisional Application No. 62/163,511 filed May 19, 2015 and U.S. Provisional Application No. 62/274,958 filed Jan. 5, 2016. The disclosures of such international patent application and U.S. priority patent applications are hereby incorporated herein by reference in their respective entireties for all purposes.

TECHNICAL FIELD

The present disclosure relates to methods for agent delivery into the eggs and embryos of egg-producing aquatic animals. The subject matter of the invention includes methods used to enhance chorion permeability and administer agents, e.g., large molecules, into the eggs and embryos. The present disclosure also relates to methods for drug and bioactive agent screening in safety and toxicity assays for biotech and pharmaceutical industries, and the production of reproductively sterile fish for aquaculture, the aquarium trade, and control of invasive species.

The disclosure further includes methods used to administer Morpholino oligomer (MO) into eggs and embryos of egg-producing aquatic animals which lead to the failure of fertile gonad development and to sterile adult fish.

BACKGROUND ART

Aquaculture is becoming increasingly important to resolve the current and projected global shortfalls in aquatic foods and seafood availability. As the shift in dependence from fisheries' harvests to artificially propagated aquatic species continues, optimization of aquaculture methods is increasingly necessary to maximize food production and minimize ecological impact, thereby achieving long-term environmental sustainability of our seafood supplies.

Sterilization (induced infertility) of farmed fish and other egg-producing aquatic animals enhances their growth rate by increasing the conversion of food energy to muscle growth, instead of gonadal development. In addition, if escaped from aquaculture operations to the environment, reproductively sterile farmed fish and other egg-producing aquatic animals, including domesticated, non-native or genetically modified species, will not be able to reproduce or inter-breed with wild population. This will assist biological containment and prevent genetic contamination of wild populations and/or the establishment in the wild of domestic, non-native or genetically modified farmed fish and other egg-producing aquatic animals.

Additionally, reproductive sterilization of fish and other egg-producing aquatic animals prevents unauthorized breeding and sale of patented, or otherwise protected, genetically selected or modified fish and other egg-producing aquatic animals.

Furthermore, aquatic animals, such as zebrafish, have provided models for evaluation of drugs or bioactive agents of interest. However, one of the major challenges in the use of eggs and embryos of these aquatic animals is the low permeability of the chorion or egg envelope which prevents such agents from traversing the chorion and reaching the embryo.

Therefore, methods are needed to enhance the permeability of the chorion of the eggs of aquatic animals and allow candidate drugs, bioactive agents and large molecules to traverse the chorion and to reach the embryo. In addition, methods are needed for reproductive sterilization of egg-producing aquatic animals.

SUMMARY

It has been discovered that certain compounds, e.g., guanidine, arginine, and their derivatives, dimers, trimers or polymers, are able to effectively enhance permeability of the chorion of eggs of aquatic animals, which allows agents, such as candidate drugs, potentially bioactive agents and/or large molecules, to traverse the chorion of such eggs of egg-producing aquatic animals and reach the embryos.

One aspect of the disclosure relates to a method of delivering at least one agent into fertilized or unfertilized egg(s) from an egg-producing aquatic animal, the method comprising contacting the fertilized or unfertilized egg(s) with the at least one agent in the presence of a guanidine-containing compound that is effective to enhance permeability of the chorion of the egg(s). Such methods may be used in screening methods for agents of interest.

Thus, another aspect of the disclosure relates to a method of conducting drug screening and compound toxicity assays using aquatic animals, the method comprising contacting egg(s) from an aquatic animal with at least one agent comprising a drug, a drug candidate, a toxic compound or a toxic compound candidate in the presence of a guanidine-containing compound that is effective to enhance permeability of the chorion of the egg(s), the method further comprising a response in the aquatic animal to the agent.

A further aspect of the disclosure relates to a method of enhancing permeability of the chorion of egg(s) from an egg-producing aquatic animal comprising contacting fertilized or unfertilized egg(s) from the egg-producing aquatic animal with a guanidine-containing compound capable of enhancing the permeability of the chorion of the egg(s).

The disclosure further relates to methods of producing populations of sterile egg-producing aquatic animals, wherein the sterilization methods include disruption of primordial germ cell migration and/or development in each treated individual without detrimentally affecting other characteristics of a normal animal.

A yet further aspect of the disclosure relates to a method of producing reproductively sterile egg-producing aquatic animals, said method comprising contacting fertilized egg(s) with anti-sense Morpholino oligomer selected from oligomer sequences comprising 12 bases that is effective to transfect the egg(s) and render individual(s) produced therefrom reproductively sterile.

Yet another aspect of the disclosure relates to a method of producing reproductively sterile egg-producing aquatic animals, said method comprising contacting fertilized egg(s) immediately after fertilization with anti-sense Morpholino oligomer that is effective to transfect the egg(s) and render individual(s) produced therefrom reproductively sterile.

Other aspects, features and advantages of the invention will be more fully apparent from the ensuing disclosure and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 shows bright field photographic results that high concentration of poly-arginine/9 mer (100 μM) generated uncharacterized aggregates within 1 hour of incubation and caused chorion lysis after 18 hours incubation, which were not seen in the 10 μM poly-arginine/9 mer treated group.

FIG. 6A shows bright field photographic results with poly-arginine and fluorescein-dextran; FIG. 6B shows bright field photographic results with fluorescein-dextran alone. FIG. 6C shows the fluorescently photographic results with poly-arginine and fluorescein-dextran; FIG. 6D shows the fluorescently photographic results with fluorescein-dextran alone.

(FIG. 7B) well-developed ovary of untreated female fish; (FIG. 7C) the gonads of salmonids' dnd-MO-Vivo treated fish developed into a thin filament-like tissue; (FIG. 7D) a photomicrograph of dissected gonads; (FIG. 7E) the active spermatogenesis of the testis of an untreated male fish; (FIG. 7F) a well-developed ovary of an untreated control female with oocytes at different developmental stages; (FIG. 7G) histological examinations of gonadal tissue show the gonad of a salmonids' dnd-MO-Vivo treated fish appears to be under-developed without advanced gonadal structure or germ cells.

(FIG. 8B) a developing ovary of untreated female; (FIG. 8C) the gonads of dnd-MO-Vivo treated or dnd-MO treated fish developed into a thin filament-like tissue; (FIG. 8D) a photomicrograph of dissected gonads from (A), (B) and (C).

FIG. 9 shows guanidine-containing compounds of general formulas (I) to (IV).

DETAILED DESCRIPTION OF THE DISCLOSURE

Figure 1:
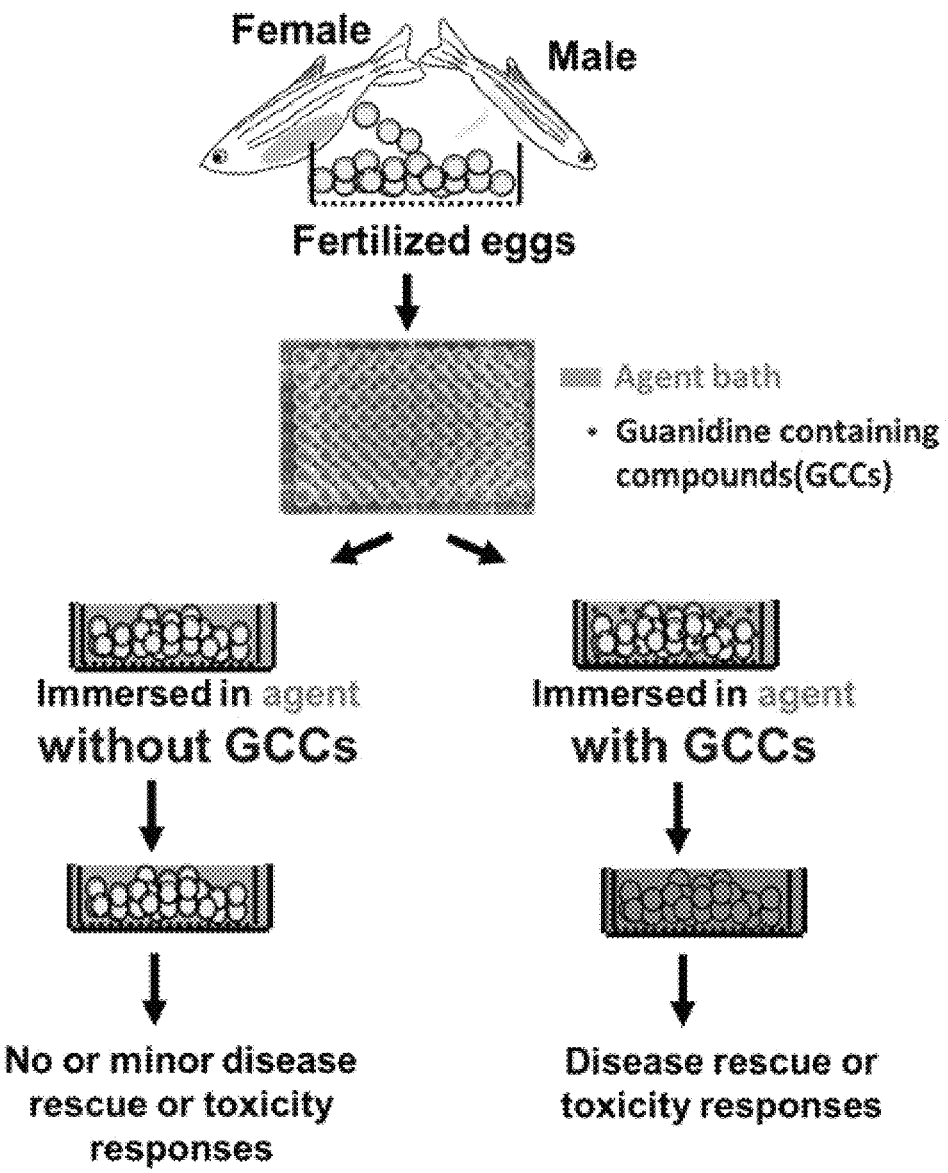
FIG. 1 is a flow chart diagram of the drug screening or agent toxicity assays performed according to embodiments of the disclosure that use guanidine-containing compound(s) (GCCs) to enhance chorion permeability.

In one aspect, the disclosure relates to a method of enhancing the permeability of the chorion of egg(s) from an egg-producing aquatic animal comprising contacting fertilized or unfertilized egg(s) from the egg-producing aquatic animal with a guanidine-containing compound capable of enhancing the permeability of the chorion of the egg(s). Such method allows for delivery of agents of interest to the embryo by enhancing the permeability of the chorion sufficiently to allow the agent to access to the interior of the egg.

Delivery of agents into fish or other egg-producing aquatic animals has traditionally been achieved via the feed, injection, or immersion of embryos or individuals in an agent of interest. Injection of stock, however, is not practical in large-scale commercial aquaculture operations. In addition, use of immersion treatment of fertilized and water-activated eggs has been limited due to low permeability of the chorion of the egg, a thick acellular multi-layer coat, also known as the egg envelope, composed mainly of proteins and glycoproteins. Typically, in immersion treatment of fish or other egg-producing aquatic animal embryos, agents of interest, by way of example, such as large molecular compounds, are not able to traverse the chorion and reach the embryo.

After ovulation/spawning and prior to fertilization and water-activation, eggs have a permeable and perforated chorion (or outermost coat) that allows for entry of water and substances into the unfertilized eggs through the pores or the micropyle, a small canal in the chorion of the egg allowing for the sperm to penetrate the egg for fertilization. Following fertilization and water-activation, however, the chorion becomes sealed and the egg is rendered substantially impermeable, preventing further uptake of substances or water from the environment.

The methods of the disclosure provide for enhancing the permeability of the chorion of egg(s) of an egg-producing aquatic animal, either a fertilized or an unfertilized egg, such that delivery of at least one agent into egg(s) from an egg-producing aquatic animal may be achieved. Such methods comprise contacting fertilized or unfertilized egg(s) from the egg-producing aquatic animal with at least one agent in the presence of a guanidine-containing compound (GCC) capable of enhancing the permeability of the chorion of the egg(s).

The contacting of fertilized or unfertilized egg(s) comprises chorionic transfection of the egg(s).

The guanidine-containing compound in aspects of the disclosure may be chosen from guanidine, guanidine derivatives, guanidine dimers, trimers or polymers, e.g. dendrimers, or salts thereof, or arginine, arginine derivatives, arginine dimers, trimers or polymers, e.g. dendrimers, or salts thereof containing a guanidine moiety, and mixtures thereof.

The guanidine-containing compounds suitable for use in the disclosed methods are guanidine-containing compounds effective to enhance the permeability of the chorion of egg(s) of aquatic animals. As used herein "effective to enhance the permeability of the chorion" means that after an egg of an aquatic animal is contacted with the guanidine-containing compound, the chorion of such egg is more permeable than the chorion of an egg of such aquatic animal not contacted with the guanidine-containing compound. By way of example, the permeability of the chorion of an egg of an aquatic animal after contact with a guanidine-containing compound at time T1 would be more permeable than the chorion of an egg of the same aquatic animal not contacted with the guanidine-containing compound at time T1. The permeability may be determined by methods known to those in the art; see, for example, Hagedorn, M., et al. (1997) "Water distribution and permeability of zebrafish embryos, Brachydanio rerio" *J Exp Zool* 278, 356-371; and Kais, B., et al., (2013) "DMSO modifies the permeability of the zebrafish (Danio rerio) chorion-implications for the fish embryo test (FET)," *Aquat Toxicol*, 140-141: p. 229-38.

As used herein, the term "derivatives" is intended to mean derivatives comprising the same functional structure as the compound they are referring to, and that have similar properties, e.g., are effective to enhance the permeability of the chorion of egg(s) of aquatic animals.

As used herein "guanidine" means any compound comprising in its chemical formula at least one carbon atom doubly bonded to a nitrogen atom and singly bonded to two other nitrogen atoms and includes salts of such compounds.

The guanidine-containing compound, in one aspect, may be selected from the compounds of general formula (A) below:

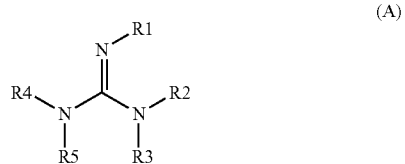

wherein:
R1, R2, R3, R4 and R5 represent, independently: a hydrogen atom, nitro, amino, cyano, phenyl, cyclohexyl, benzyl, or a linear or branched $C_1$-$C_4$ lower alkyl or $C_1$-$C_4$ alkenyl radical, optionally substituted with one or two radicals chosen from: hydroxyl, amino, dimethylamino, methoxy, ethoxy, carboxyl, carboxamide, N-methylcarboxamide or $SO_3H$, or salts thereof.

Examples of guanidine-containing compounds include arginine, guanidine-HCl, guanidine-thiocyanate, guanidine-acetate, guanidine-carbonate, guanidine-nitrate, guanidine-sulfate, guanidine-bicarbonates and guanidine-hydrobromides.

In other aspects, the guanidine-containing compound is a guanidine-containing dimer, trimer or polymer. In one aspect, the guanidine-containing compound may be selected from the compounds of general formulas (I) to (IV) shown in FIG. 9.

The variable group "R" may be selected from a hydrogen atom, nitro, amino, cyano, phenyl, cyclohexyl, benzyl, or a linear or branched $C_1$-$C_4$ lower alkyl or $C_1$-$C_4$ alkenyl radical, optionally substituted with one or two radicals chosen from: hydroxyl, amino, dimethylamino, methoxy, ethoxy, carboxyl, carboxamide, N-methylcarboxamide or $SO_3H$, or salts thereof. The variable backbone linker may be selected from an amino acid, nucleotide, phosphoramidate, glycol, polyethylene glycol, nitro, amino, cyano, phenyl, cyclohexyl, benzyl, or a linear or branched $C_1$-$C_4$ lower alkyl. By way of example, polyarginine/9-arginine is a compound of formula I with n=9.

The guanidine-containing compounds may be used in methods of delivering at least one agent into fertilized or unfertilized egg(s) from an egg-producing aquatic animal, said method comprising contacting the fertilized or unfertilized egg(s) with the at least one agent in the presence of a guanidine-containing compound that is effective to enhance permeability of the chorion of the egg(s).

The agent may be any compound, drug or drug candidate, bioactive agent or potentially bioactive agent, pharmaceutical, chemically active substance, therapeutic substance, or other test substance. These include, without limitation, forms such as uncharged molecules, molecular complexes, salts, ethers, esters, amides, etc.

By way of example, the agent or agents may be placed in an immersion medium containing the fertilized or unfertilized egg(s) and the guanidine-containing compound(s) such that the agent(s) is in the presence of the guanidine-containing compound.

The guanidine-containing compounds are either covalently bound or not covalently bound to the agent(s) in the methods of the disclosure. It has been discovered that the guanidine-containing compounds are capable of enhancing the permeability of the chorion of egg(s) from an egg-producing aquatic animal and allowing for delivery of agents to the embryo even where the guanidine-containing compounds are not covalently bound to or conjugated with the agent.

The guanidine-containing compound according to some aspects of the disclosure can be a dendrimer, e.g. an octaguanidine dendrimer comprising a triazine core moiety e.g., of a type as described in U.S. Pat. No. 7,935,816, also known in the art as "Vivo". The disclosure of U.S. Pat. No. 7,935,816 is hereby incorporated herein by reference in its respective entirety. In certain embodiments of the disclosure where the guanidine-containing compound is an octaguanidine dendrimer comprising a triazine core moiety, the guanidine-containing compound is not covalently bound to or conjugated with the agent(s) of interest.

The immersion medium in embodiments is an aqueous medium. The immersion medium may be any such medium known to those of skill in the art for use with eggs from aquatic animals. The immersion media, for example, may be an aqueous medium which may further comprise fresh water, brackish water, sea water, fish ovarian fluid or fertilization diluent that contains salt, Tris (pH 7-9), glycine, and/or 0 to 30% of serum and protease inhibitors such as aprotinin or leupeptin.

The concentration of the guanidine-containing compound in the immersion medium is an amount sufficient for enhancing the permeability of the chorion of the eggs in the immersion medium. By way of example, the concentration of the guanidine-containing compound may be in a range of from about 1 to about 80,000 µM, preferably in the range of from about 20 to about 40,000 µM, and more preferably in the range of from about 40 to about 20,000 µM.

The discovery that guanidine-containing compounds according to the disclosure are able to effectively enhance permeability of the chorion of eggs of aquatic animals provides the ability to efficiently deliver agents to the eggs and embryos of aquatic animals. The delivery of agents further allows for use of aquatic animals in models for drug or bioactive agent screening or in assays for evaluation of toxicity of a test agent. By way of example, zebrafish have been used in phenotypic models for drug or bioactive agent screening. Accordingly, the methods disclosed herein may be used, for example, in drug or bioactive agent screening methods, assays for assessing drug or bioactive agent safety or toxicity, and methods for evaluating a test agent for biological response.

FIG. 1 illustrates one example of the application of guanidine-containing compounds in drug screening or agent toxicity assays. As shown, fertilized eggs are placed in an agent bath. One group of eggs is immersed in the agent bath without guanidine-containing compounds therein and one group of eggs is immersed in the agent bath in the presence of guanidine-containing compounds. The therapeutic or toxicity responses of the eggs immersed in compound with GCCs can be monitored and/or evaluated.

Aspects of the disclosure thus encompass a method of screening a test agent such as a drug or bioactive agent, e.g.

antibody, protein, peptide, RNA or DNA, comprising contacting egg(s) from an egg-producing aquatic animal with the at least one agent in the presence of a guanidine-containing compound that is effective to enhance the permeability of the chorion of the egg(s) and identifying a response, e.g., a physiological response. By way of example, the screening method may be used to evaluate the test agent, evaluate the effects of the test agent on the fish embryo, evaluate the toxicity of the test agent, etc.

The methods of disclosure additionally encompass use of guanidine-containing compounds in compound safety and toxicity assays wherein a test agent is placed in contact with egg(s)/embryo(s) from an egg-producing aquatic animal in the presence of a guanidine-containing compound that is effective to enhance the permeability of the chorion of the egg(s)/embryo(s) and identifying a response, e.g., a disease rescue or a physiological response (abnormality and mortality) and the response to the test agent is monitored and evaluated.

The disclosure further contemplates methods of producing reproductively sterile egg-producing aquatic animals involving contacting eggs in immersion medium with selected agents resulting in reproductively sterile individuals. The sterilization methods comprise the disruption of gonadal development in the embryo. The present disclosure also relates to methods of preventing interbreeding between domesticated, non-native and genetically modified farmed fish/other egg-producing aquatic animals and their wild stocks, as well as to the establishment of such aquacultured fish and other egg-producing aquatic animals in the wild. In addition, the disclosed methods may be employed to enable prevention of genetic contamination of a wild population by farmed fish and other egg-producing aquatic animals.

As defined herein, "sterilizing" egg-producing aquatic animals is understood to mean rendering an individual unable to sexually reproduce. Reproductively sterile egg-producing aquatic animals are defined as individuals that are unable to reach sexual maturity or to reproduce when reaching the age of sexual maturity.

The disclosure thus provides a method of producing reproductively sterile egg-producing aquatic animals, the method comprising contacting egg(s) with an agent that is effective to transfect the egg(s) and render individual(s) produced therefrom reproductively sterile. In some aspects, the agent is contacted with the eggs in the presence of a guanidine-containing compound. In some aspects, the agent is an anti-sense Morpholino oligomer.

The methods of producing a reproductively sterile fish and other egg-producing aquatic animals include administration of agents to their eggs to disrupt primordial germ cell (PGC) development, migration and colonization in the gonad of the embryo, which results in failure of gonad development and/or failure of full and proper gonadal functioning at the cellular or tissular level, and ultimately the generation of sterile fish and other egg-producing aquatic animals.

PGCs are a population of cells in the fish embryo that are precursors of the gametes of the adult fish and other egg-producing aquatic animals. The PGCs are produced during the very early stages of embryonic development. At later stages of embryonic development, the PGCs migrate through the embryo from their original location to the area of the gonadal precursors. At the end of their migration, the PGCs enter the developing gonads, colonize the tissue and start the process of gametogenesis, leading to mature gonads in the adult fish and other egg-producing aquatic animals.

The methods of the disclosure allow generation of reproductively sterile (infertile) egg-producing aquatic animals. The sterilization strategy will specifically disrupt gonad development in the individuals without detrimentally affecting any other characteristics resulting in the production of completely normal but reproductively sterile egg-producing aquatic animals.

Thus, in various embodiments, the disclosure provides a method to efficiently administer agents into embryos by contacting eggs with agents suitable to disrupt PGC development, migration and/or survival in large numbers of embryos, resulting in large-scale production of reproductively sterile adult fish and other egg-producing aquatic animals. The methods of the disclosure are also applicable to single embryos in smaller scale production of reproductively sterile adult fish and other egg-producing aquatic animals.

Figure 2:
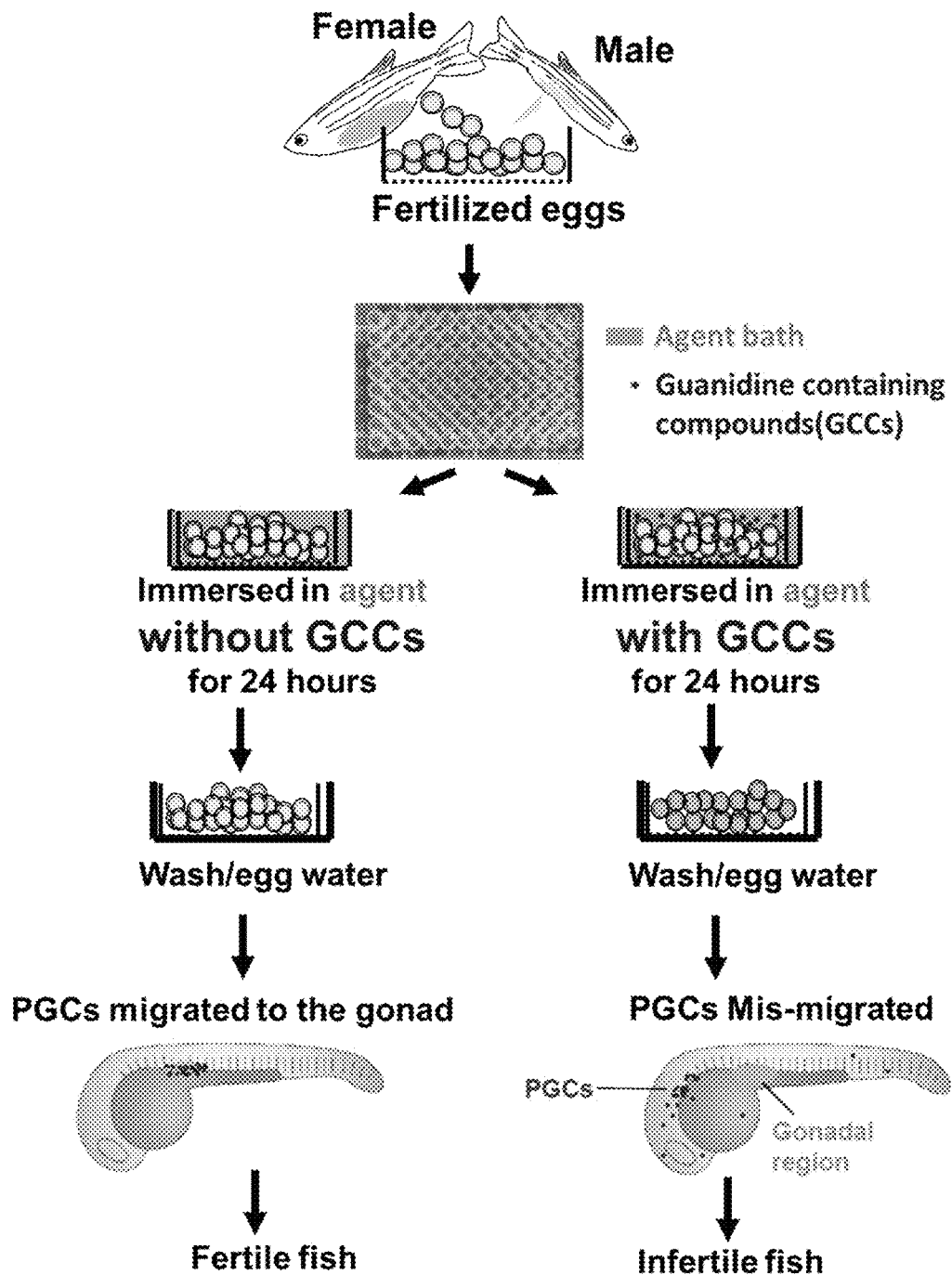
FIG. 2 is a flow chart diagram of the production of reproductively sterile fish obtained according to embodiments of the disclosure that use guanidine-containing compound(s) (GCCs) to enhance chorion permeability.

In some aspects, the agent administered to render the individual(s) produced therefrom reproductively sterile is delivered into the eggs in the presence of a guanidine-containing compound according to this disclosure. FIG. 2 illustrates an example of the application of guanidine-containing compounds in the production of infertile fish. As shown in FIG. 2, fertilized eggs are either immersed in an agent bath containing guanidine-containing compound(s) or not containing any GCCs. The eggs are immersed in the bath for 24 hours and then washed. The eggs immersed in the bath with the GCC(s) resulted in infertile fish due to mis-migration of the PGCs, whereas the eggs immersed in the bath without the GCCs resulted in fertile fish.

The agents for use in the methods of the disclosure may include agents known to disrupt PGC development, migration and/or survival which are capable of entering the chorion of a fertilized or unfertilized egg or are provided in the presence of a compound that assists in the entering of the egg. In one aspect, such agent may be an antisense Morpholino oligomer capable of the disruption of PGC development and capable of traversing the chorion of eggs. Thus, in some embodiments, antisense Morpholino oligomer useful in the methods of the disclosure is anti-sense Morpholino oligomer that is effective to transfect the egg(s) and render individual(s) produced therefrom reproductively sterile.

Antisense Morpholino oligomer is used to transiently silence gene expression by either blocking translation or RNA splicing that is an essential step to generate mRNA. Specific antisense Morpholino oligomers can be identified to transiently block or suppress the expression of genes that are essential for embryonic germ cell development including but not limited to dead end (dnd), nanos, vasa, gnrh or fsh receptor which results in the failure of gonadal development and ultimately generates sterile fish and other egg-producing aquatic animals.

Thus, in one aspect of the disclosure, a method of producing reproductively sterile egg-producing aquatic animals is provided comprising contacting fertilized or unfertilized egg(s) with anti-sense Morpholino oligomer that is effective to transfect the egg(s) and render individual(s) produced therefrom reproductively sterile. The contacting may in some aspects include the presence of a guanidine-containing compounds according to the disclosure herein. The contacting comprises chorionic transfection of the egg(s). The contacting may be at the time of water-activation.

In such aspect, the disclosure relates to methods of producing reproductively sterile egg-producing aquatic animals by administration of effective Morpholino oligomers to eggs in order to disrupt primordial germ cell (PGC) development, and migration to, and colonization in, the gonad of the embryo, which results in the failure of gonad development and/or full and proper gonadal functioning at the cellular or tissural level, and ultimately the generation of sterile fish.

Dead end (dnd) is a vertebrate-specific component of the germ plasm and germ-cell granules that is essential for germ cell development. The dnd gene is specifically expressed in germ plasm and primordial germ cells. Since dnd is considered essential for normal migration and survival of PGCs, embryos devoid of this protein develop to become sterile adults.

The disclosed methods are useful for the production of reproductively sterile fish and other egg-producing aquatic animals for aquaculture, the aquarium trade, and control of invasive species. In one aspect, the methods include disruption of gonadal development through the administration of antisense Morpholino oligomer against dead end mRNA (dnd-MO) or other genes that are essential to gonadal development including, but not limited to, nanos, vasa, gnrh or fsh receptor, to fertilized egg(s). The action of dnd-MO or other antisense Morpholino oligomer against genes that are essential to gonadal development leads to the failure of fertile gonad development and to sterile adult fish.

In embodiments, the dnd-MO is able to transiently suppress expression of Dead end protein that is essential for embryonic germ cell development.

The present disclosure also relates to specific Morpholino oligomer sequences for use in methods for suppression of expression a dead end gene in a fish.

Figure 3:
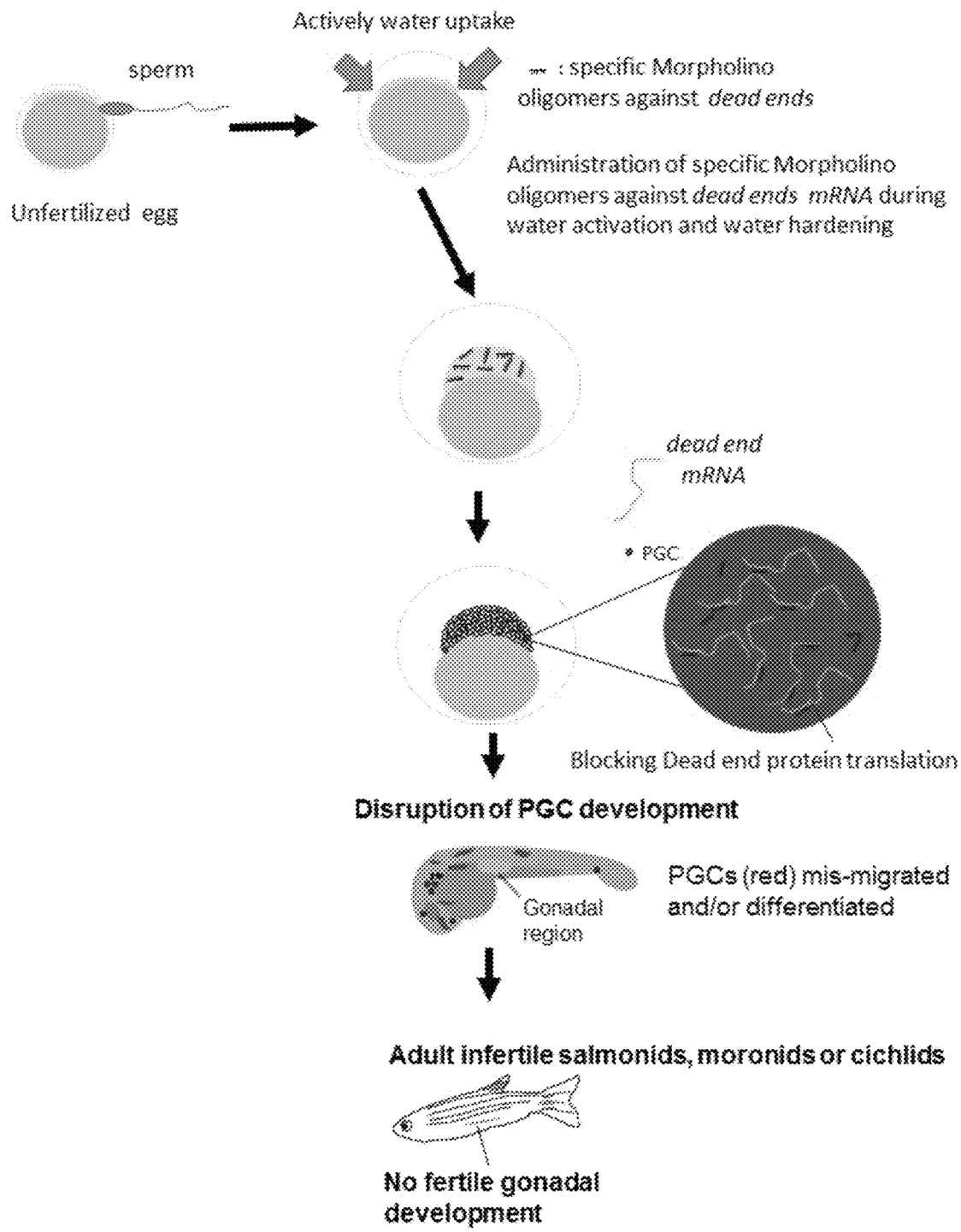
FIG. 3 is flow chart diagram of the production of reproductively sterile fish obtained according to embodiments of the disclosure.

FIG. 3 is a flow chart for production of reproductively sterile fish by the administration of specific Morpholino oligomers against the dead end mRNAs of fish to disrupt primordial germ cell (PGC) development, which results in the failure of gonad development, and ultimately the generation of sterile fish. When eggs are not treated with Morpholino oligomers, they may become fertile broodstock.

As shown in FIG. 3, eggs of fish (e.g. from salmonids, moronids or cichlids) are contacted with Morpholino oligomers against the dead end genes of the relevant fish species. FIG. 3 illustrates the administration of Morpholino oligomers against the dead end genes during water activation and water hardening. Alternatively, the eggs may be given no treatment. As shown, where the eggs are contacted with Morpholino oligomers, oligomers effect the suppression of or blocking of Dead end protein translation, resulting in the disruption of PCG development. The adult fish are consequently infertile, since there is no fertile gonadal development. When normal PGC development is permitted, the fish will have normal fertile gonadal development and the fish may be used as broodstock.

Thus, in embodiments, the antisense Morpholino oligomers are capable of effectively suppressing expression of at least one dead end gene, e.g. of at least one dead end gene of Salmonidae dead end gene, Moronidae dead end gene or Cichlidae dead end gene.

In another aspect, the disclosure relates to specific antisense Morpholino oligomers that are able to transiently and effectively suppress the translation of dead end, an essential gene for germ cell survival, and specifically disrupt gonadal development resulting in the production of infertile fish, e.g., salmonids (salmons and trouts), moronids (basses) and cichlids (tilapias and ornamental cichlids).

In another aspect, the disclosure relates to the identification of short sequences of Morpholino oligomer that can be more easily up-taken by eggs to reach target cells. Such short sequences preferably are 12 bases or 18 bases instead of 25 bases, as disclosed in WO 2015/073819, incorporated herein by reference. Such Morpholino oligomer sequences have been found to more efficiently transiently block the expression of specific genes that are essential for germ cell development in cold water species such as Atlantic salmon. The low egg hatching temperature is believed to make short Morpholino oligomers more stable against its target mRNA to transiently block the expression of specific genes.

The disclosure further relates to a specific Morpholino oligomer, 5'-ACGCTCCTCCAT-3' (SEQ ID NO: 1) and its variants, e.g., 5'-ACTTGAACGCTCCTCCAT-3' (SEQ ID NO: 2), that are able to transiently and effectively suppress the expression of Salmonidae dead end gene, which results in the failure of gonad development and/or the failure of full and proper gonadal functioning, and ultimately the generation of sterile salmonids. Accordingly, the methods of the disclosure are applicable to all salmonids, including, but not limited to, Atlantic, coho, chinook, chum, sockeye, pink and masu salmons, rainbow, brook and brown trouts, common and Arctic grayling, and Arctic char, among others.

The Morpholino oligomers may be variants of the listed sequences. These variations may include but not be limited to other modified nucleic acids and other Morpholino oligomers that cover the whole or partial sequences listed above. Particularly included are antisense oligomers that comprise, consist essentially of, or consist of, one or more of SEQ ID NO:1 and SEQ ID NO: 2. Also included are variants of these antisense oligomers, including variant oligomers having 80%, 85%, 90%, 95%, 97%, 98%, or 99% (including all integers in between) sequence identity or sequence homology to any one of SEQ ID NO:1 and SEQ ID NO: 2, and/or variants that differ from these sequences by about 1, 2, 3, 4, 5, 6, 7, 8, 9, or 10 nucleotides, preferably variants that are effective in reproductively sterilizing fish upon contact with fish egg(s).

Another aspect of the invention includes antisense Morpholino oligomers which consist of SEQ ID NO: 1 and variants thereof. Yet another aspect of the invention includes transfected eggs of an egg-producing aquatic animal comprising an anti-sense Morpholino oligomer which consists of the nucleotide sequence of SEQ ID NO: 1 or a variant thereof.

Variants that are effective in reproductively sterilizing fish upon contact with fish egg(s) as used in such context means use of the variants in the methods disclosed herein will result in reproductively sterile fish. In embodiments, the variants will effectively suppress the expression of a dead end gene of interest.

According to embodiments of the methods of the disclosure, fertilized or unfertilized fish egg(s) (one or more eggs) are immersed in an immersion medium comprising an antisense Morpholino oligomer effective to suppress expression of a dead end gene in the fish of interest. Such immersion is preferably at the start of water activation of the egg(s). The concentration of the antisense Morpholino oligomer in the immersion medium should be sufficient to allow the antisense Morpholino oligomer to traverse the chorion of the fish egg(s), effectively transfecting the egg(s). In embodiments, such concentration will typically be about 1 to about 200 µM, more preferably, about 10 to about 100 µM, and still more preferably, about 20 to about 60 µM.

The immersion medium, by way of example, is typically an aqueous medium which may further comprise fresh water, brackish water, sea water, fish ovarian fluid or fertilization diluent that contains salt, Tris (pH 7-9), Glycine, and/or 0 to 30% of serum and protease inhibitors such as aprotinin or leupeptin.

In accordance with the disclosure, the immersion medium may further comprise a guanidine-containing compound as detailed above capable of enhancing the permeability of the chorion of the eggs(s).

Although the time required for the immersion of the fertilized eggs to result in satisfactory sterilization of the fish or other egg-producing aquatic animals will depend on the species of fish and other egg-producing aquatic animals, typically the fish or other eggs will be immersed in the immersion medium containing a Morpholino oligomer and, optionally, a guanidine-containing compound for about 2 to about 96 hours, more preferably for about 4 to about 72 hours, and still more preferably from about 5 to about 48 hours.

In one aspect, the disclosure relates to methods of producing reproductively sterile fish and other egg-producing aquatic animals by administration of guanidine dendrimers to either fish eggs or embryos in order to disrupt primordial germ cell (PGC) development and migration to, and colonization in, the gonad of the embryo, which results in the failure of gonad development and/or the failure of full and proper gonadal functioning at the cellular or tissular level, and ultimately the generation of sterile fish and other egg-producing aquatic animals.

In one aspect, the disclosure relates to a guanidine dendrimer comprising a triazine core, e.g. an octaguanidine dendrimer with a triazine core, also known in the art as "Vivo". Such compounds are described in U.S. Pat. No. 7,935,816. The disclosure of U.S. Pat. No. 7,935,816 is hereby incorporated herein by reference in its respective entirety.

An illustrative octaguanidine dendrimer transporter compound with morpholino as a representative agent is shown in the following conjugate:

The disclosure further relates to the use of an octaguanidine dendrimer with a triazine core. Such a guanidine dendrimer is effective for chorionic transport of a Morpholino oligomer, either covalently bound to the Morpholino oligomer or not covalently bound to the Morpholino oligomer.

In another aspect, the disclosure contemplates a method of producing reproductively sterile egg-producing aquatic animals, said method comprising contacting fertilized egg(s) (or embryos) with anti-sense Morpholino oligomer and a guanidine dendrimer that is effective to transfect the egg(s) and render individual(s) produced therefrom reproductively sterile.

The selected Morpholino oligomers may disrupt PGC development, migration and/or survival in large numbers of embryos, resulting in large-scale production of reproductively sterile adult fish and other egg-producing aquatic animals. The methods of the disclosure are also applicable to single embryos in smaller scale production of reproductively sterile adult fish and other egg-producing aquatic animals.

In one embodiment, a method of producing reproductively sterile egg-producing aquatic animals is provided, comprising immersing fertilized or unfertilized fish egg(s) in an immersion medium comprising a guanidine dendrimer, e.g. Vivo, and an antisense Morpholino oligomer capable of effectively suppressing expression of the dead end gene or other genes such as nanos, vasa, gnrh or fsh receptor that are essential for gonadal development in the fish and other egg-producing aquatic animals Preferably, the guanidine dendrimer is an octaguanidine dendrimer with a triazine core, e.g. Vivo. The antisense Morpholino oligomer may, by way of example, be SEQ ID NO: 1 or SEQ ID NO: 2.

According to particular aspects of the methods of the disclosure, fertilized or unfertilized egg(s) (one or more) are

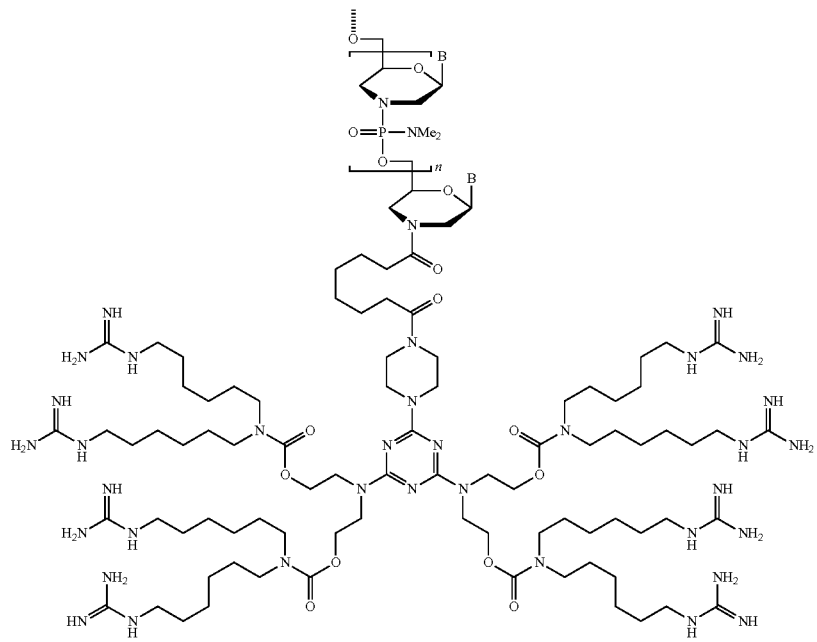

A particular guanidine dendrimer that is useful with morpholino oligomers of the disclosure is 2-[(4-nitrophenyl)oxycarbonylhexamethylenecarbonylpiperazinyl]-4,6-bis{di-[di(trifluoroacetamidohexyl)aminocarbonyloxy-ethyl]amino}triazine.

immersed in an immersion medium comprising a guanidine dendrimer and an antisense Morpholino oligomer capable of effectively suppressing the expression of a dead end gene or other genes that are essential for gonadal development in the fish and other egg-producing aquatic animals. The concentration of the antisense Morpholino oligomer in the immersion medium should be sufficient to allow the antisense Morpholino oligomer to traverse the chorion of the egg(s). In embodiments, such concentration will typically be about 1 to about 200 µM, more preferably about 10 to about 100 µM, even more preferably from about 20 to about 60 µM.

All aspects of the disclosure may include the administration or use of guanidine-containing compounds effective to enhance the permeability of the chorion of an egg from an aquatic animal. In such aspects, the guanidine-containing compounds are either covalently bound or not covalently bound to any agent intended to transfect the chorion of the egg.

It will be recognized that the contacting of eggs and/or embryos with the agents and compounds of the present disclosure may be carried out in any suitable manner, e.g., involving immersion contacting, or alternatively by contacting not involving immersion, although it is to be recognized that immersion contacting provides an efficient and effective contacting technique that is amenable to large-scale operations for the production of reproductively sterile fish and aquatic animals. Non-immersion contacting techniques that may be utilized in the broad practice of the present disclosure include, without limitation, spray or drip methods for contacting, dry transfer techniques, in which eggs are contacted with a carrier or surface coated with or otherwise supporting any of the agents or compounds of the present disclosure that are effective for production of reproductively sterile fish, or other techniques by which the eggs and/or embryos are contacted with the agents or compounds of the present disclosure. The contacting preferably comprises a non-injection contacting.

The present disclosure relates in one aspect to delivering agents to eggs from fish or other egg-producing aquatic animals by contacting the eggs with the agents during water activation and water hardening of fertilized eggs (FIG. 3). During this period, the eggs actively up-take water (by way of example, up to 14.83±2.05 microliter per Atlantic salmon egg). This active water-uptake force can be used to administer agents, for example, Morpholino oligomers into the eggs.

The present disclosure in some aspects describes methods of efficiently delivering agents into eggs of egg-producing aquatic animals by contacting the eggs with agents of interest during a window of time starting at water activation and water hardening. In various embodiments, the contacting comprises immersion of the eggs in an immersion medium containing one or more agent(s) of interest. As used herein, water activation and water hardening of fertilized eggs starts at the first contact of newly fertilized eggs with water to the end of water hardening.

Accordingly, in various aspects, the present disclosure relates to contacting fertilized eggs immediately starting at water-activation with an agent in immersion media. The agent used in the immersion medium may contribute to the sterilization of the egg-producing aquatic animals, and the immersion medium in specific embodiments may include additional agents or other materials that are beneficial to the egg-producing aquatic animals hatched from eggs contacted with the immersion medium, e.g., materials such as DNA/RNA, hormones, growth promoters, protective antigens, nutrients, etc.

According to particular aspects of the methods of the disclosure, fertilized egg(s) (one or more) are immersed in an aqueous immersion medium, thus starting water activation, comprising an antisense Morpholino oligomer or a guanidine-containing compound and an antisense Morpholino oligomer capable of effectively suppressing the expression of a dead end gene or other genes that are essential for gonadal development in the fish or other egg-producing aquatic animals. The immersion continues until the chorion completes the hardening process. The concentration of the antisense Morpholino oligomer in the bath should be sufficient to allow the antisense Morpholino oligomer to traverse the chorion of the egg(s). In embodiments, such concentration will typically be about 1 to about 200 µM, more preferably about 10 to about 100 µM, even more preferably from about 20 to about 60 µM.

The methods of the disclosure are applicable to egg-producing aquatic animals. As used herein, egg-producing aquatic animals include egg-bearing species of water-based animals including all fish species and other egg-producing aquatic animals such as crustaceans and/or mollusks.

Accordingly, egg-producing aquatic animals includes all fish species, including, but not limited to, salmon, Atlantic salmon, coho salmon, chinook salmon, chum salmon, sockeye salmon, pink salmon, masu salmon, trout, rainbow trout, brook trout, brown trout, common grayling, Arctic grayling, Arctic char, bass, hybrid bass, striped bass, white bass, striped-white bass hybrids, yellow bass, perch, white perch, yellow perch, European perch, bass-perch hybrids, Nile tilapia, blue tilapia, blue-Nile tilapia hybrids, Mozambique tilapia, zebrafish, carp species, breams, seabreams, porgies, catfish species, and cod.

The methods of the disclosure are additionally applicable to egg-producing aquatic animals such as crustaceans and/or mollusks. Such egg-producing aquatic animals may include, but are not limited to, shrimp, prawn, lobster, crayfish, crabs, oysters, squid, octopus, and the like.

The advantages and features of the disclosure are further illustrated with reference to the following examples, which are not to be construed as in any way limiting the scope of the disclosure but rather as illustrative of particular embodiments of the disclosure in specific applications thereof.

EXAMPLES

Zebrafish were selected for initial exemplification of the methods of the disclosure, due to their short generation time and large numbers of embryos produced per mating, which are easily obtained on a daily or weekly basis. Additionally, the embryos of zebrafish are transparent, providing ease of visual observations, and are hardy. The normal development of PGCs and gonads within the embryo is an evolutionarily conserved mechanism that is found in all fish. Accordingly, the methods of the disclosure are applicable to all fish species, including, but not limited to, zebrafish, carp species, trout species, salmon species, breams (including seabreams and porgies), basses (including marine and freshwater seabass and hybrid basses, etc), perches (yellow perch, white perch, etc), catfish species, cod and other major classes that are candidates for captive culture.

As described herein, the methods are generally applicable to farmed fish and aquatic egg-producing animals, as production of sterile farmed species is desirable. Accordingly, the methods of the invention are applicable to any farmed species of fish and aquatic egg-producing animals, particularly to commercially important farmed species.

Example 1

The disclosure relates to the specific chemicals, e.g., guanidine-containing compounds, which are able to enhance the permeability of chorion, which allows agents such as large molecules to traverse the chorion and reach the egg and embryo.

Zebrafish eggs were incubated in solutions that contained 1 µM of 10, 20 or 40 KD fluorescein-dextran with either 0 or 40 mM of arginine, guanidine-HCl or guanidine-thiocyanate for 24 hours.

Figure 4:
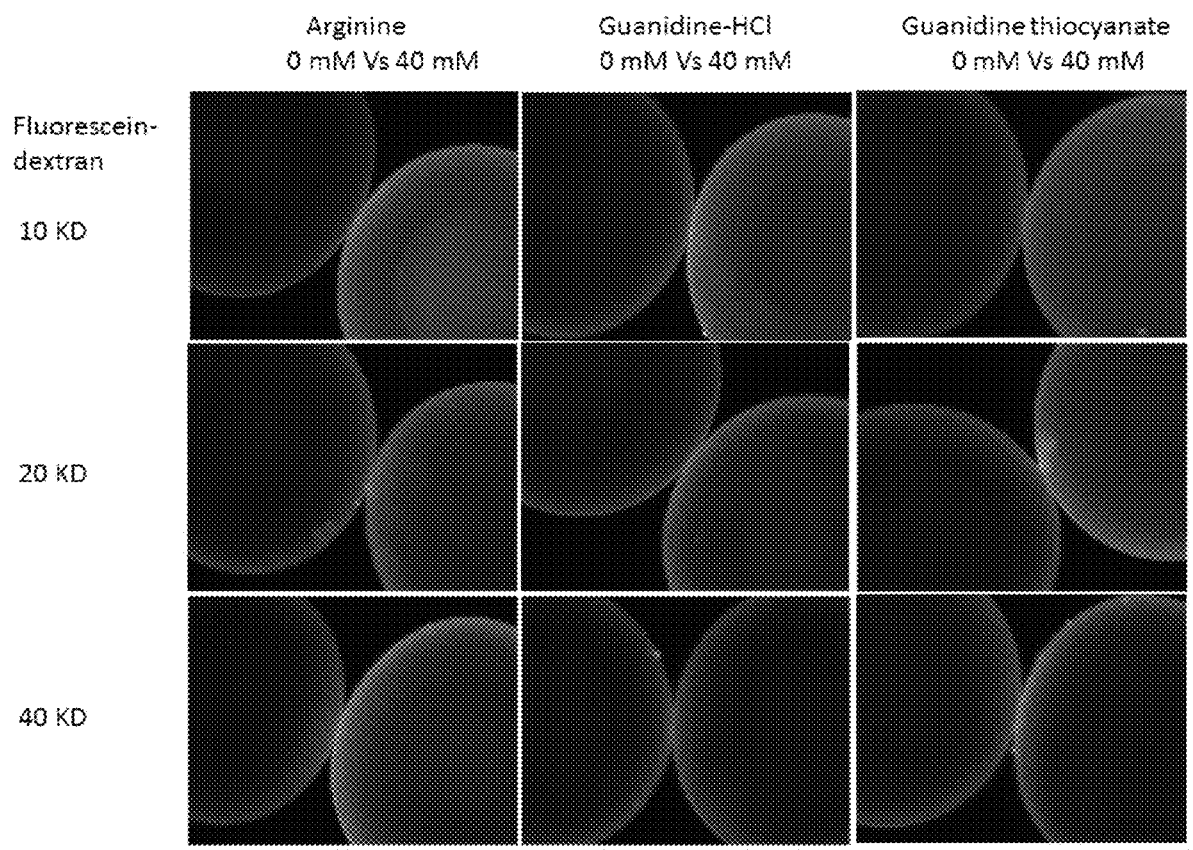
FIG. 4 is a fluorescence photomicrograph showing the effects of the administration to fish embryos of fluorescein-dextran using the GCCs arginine, guanidine-HCl and guanidine thiocyanate.

Fluorescently photographic results indicated that arginine, guanidine-HCl and guanidine-thiocyanate enhanced the uptake of fluorescein-dextran in the eggs that were treated with 40 mM of arginine, guanidine-HCl or guanidine-thiocyanate (treated eggs) over the up-take in the eggs which were incubated in solutions that did only contain fluorescein-dextran, but no guanidine-containing compounds (untreated eggs). As shown in FIG. 4, the treated eggs up-took more fluorescein-dextran than untreated eggs as indicated by higher green fluorescence found in the treated eggs. Thus, arginine, guanidine-HCl and guanidine-thiocyanate enhanced the permeability of chorion.

In addition, all three different sizes (molecule weight 10, 20 and 40 KD) of fluorescein-dextran were up-taken by the treated eggs. Accordingly, the methods of the invention are applicable to all egg-producing aquatic animals and are applicable to transfect eggs with various sized molecules, including both smaller and larger molecules.

Example 2

40 zebrafish eggs were transferred into each well of 48-well plates that contained 300 µl of fresh tank system water. After the allocation of eggs, system water in each well was replaced with 300 µl of water that contained 10 or 100 µM of poly-arginine (9-arginine polymer). After 18 hours of incubation the eggs were examined using an Axioplan 2 fluorescence microscope (ZEISS, Thornwood, N.Y., USA). The microscope is equipped with a DP70 digital camera (Olympus, Center Valley, Pa., USA).

Figure 5:
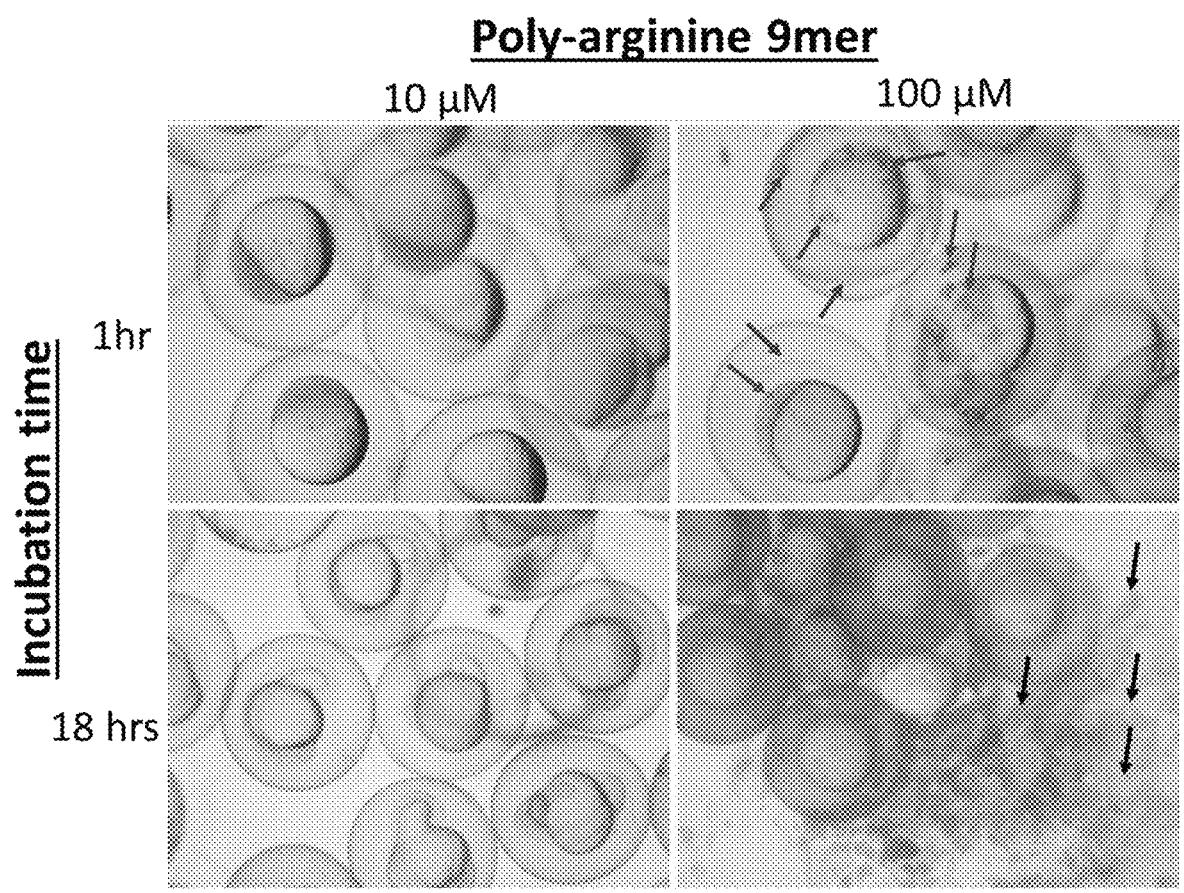
FIG. 5 is a photomicrograph showing the effects of the administration to fish embryos of poly-arginine/9mer.

FIG. 5 shows the microphotographs obtained in the study. As shown in bright field photographic results, high concentration of poly-arginine/9 mer (100 µM) generated uncharacterized aggregates with in 1 hour of incubation, which was not seen in the 10 µM poly-arginine/9 mer treated group. After 18 hours incubation, high concentration of poly-arginine/9 mer (100 µM) caused chorion lysis that was not seen in the 10 µM poly-arginine/9 mer treated group.

Example 3

40 zebrafish eggs were transferred into each well of 48-well plates that contained 300 µl of fresh tank system water. After the allocation of eggs, system water in each well was replaced with 300 µl of water that contained 0 or 40 µM of poly-arginine (9-arginine polymer) and 1 µM of 10 KD fluorescein-dextran. After 4 hours of incubation the eggs were examined using a MZ12 stereomicroscope (Leica, Buffalo Grove, USA), or an Axioplan 2 fluorescence microscope (ZEISS, Thornwood, N.Y., USA). Both microscopes were equipped with a DP70 digital camera (Olympus, Center Valley, Pa., USA).

Figures 6A, 6B, 6C, 6D:
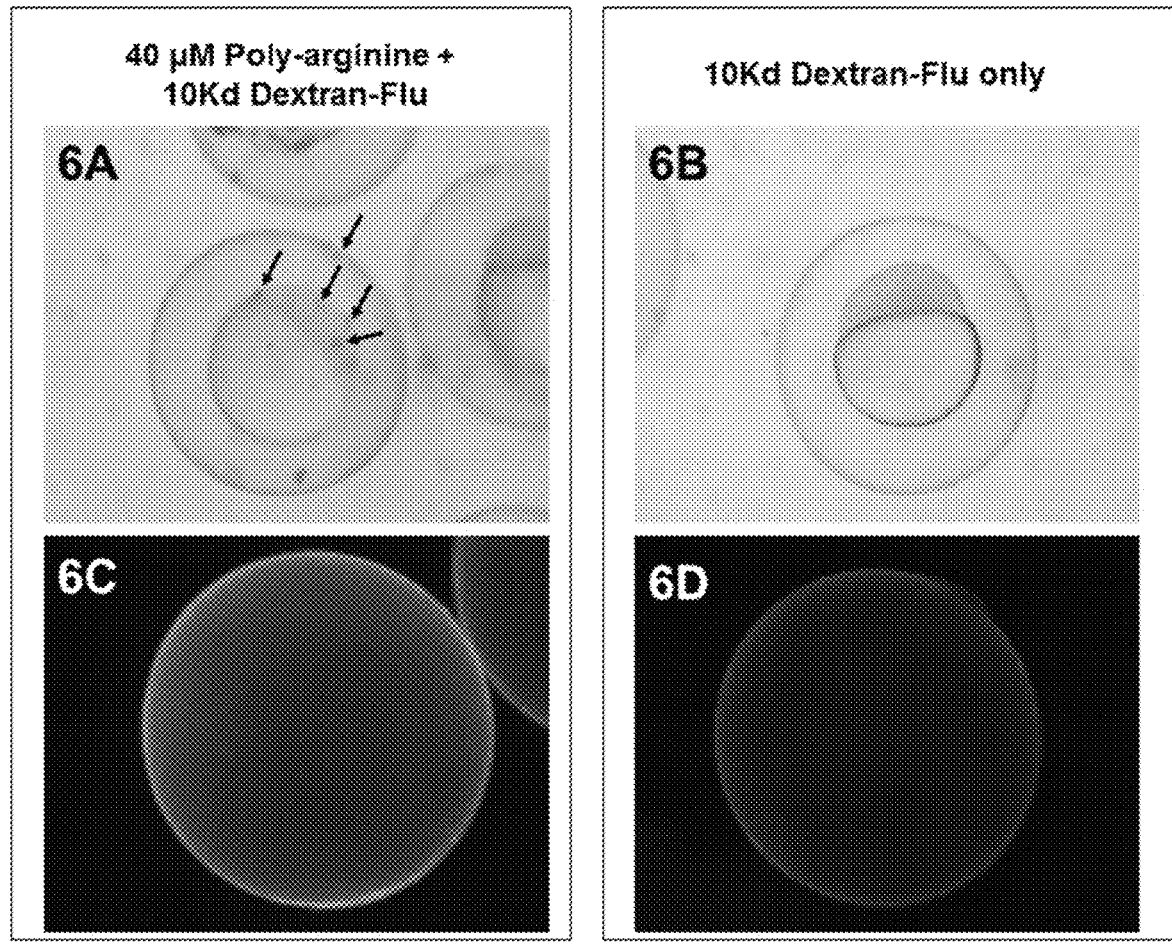
FIG. 6A-6D are photomicrographs showing the effects of the administration of fluorescein-dextran alone and in combination with poly-arginine to fish embryos.
Figures 7A, 7B, 7C, 7D, 7E, 7F, 7G:
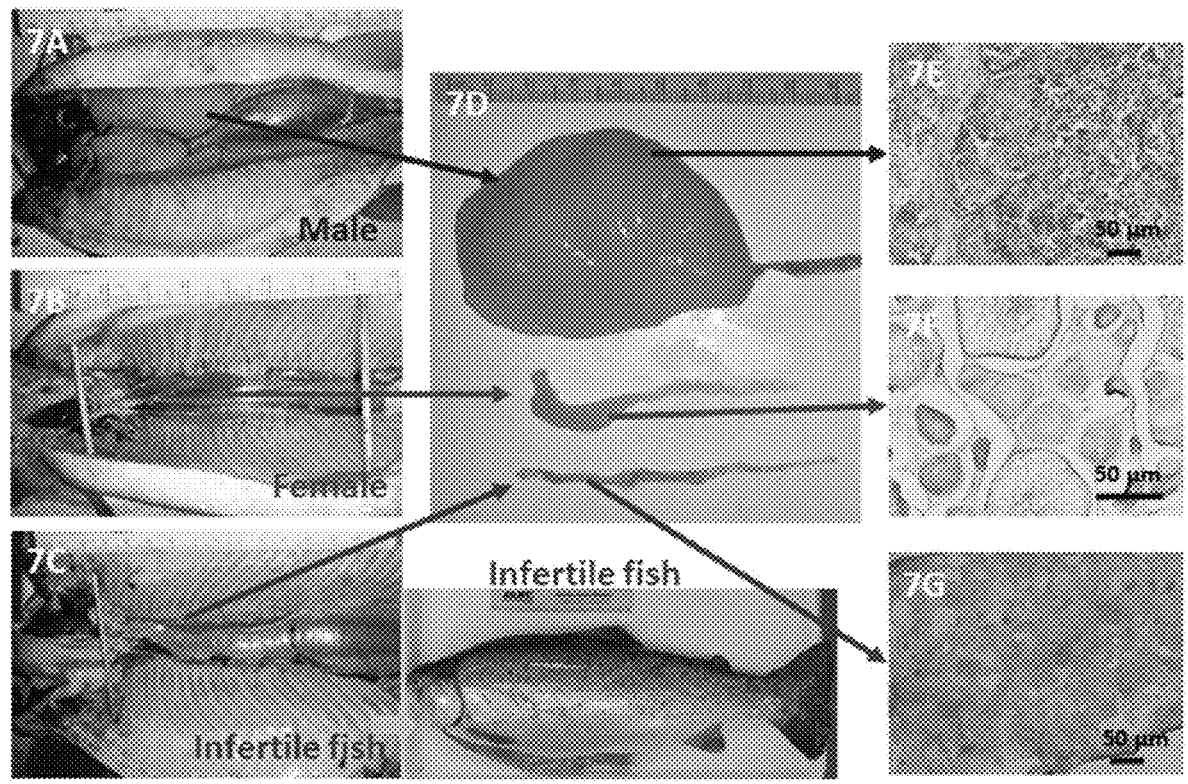
FIG. 7A-7G are photomicrographs showing salmonids' dnd-MO-Vivo induced sterility in rainbow trout. Examination of gonadal tissue show (FIG. 7A) well-developed testis of untreated male fish.

FIG. 6A-6D shows the microphotographs obtained in the study. As shown, poly-arginine enhanced the permeability of chorion. The zebrafish eggs that were incubated in solutions that contained 1 µM of 10 KD fluorescein-dextran with either 0 or 40 µM of poly-arginine are shown in FIGS. 6A and 6B. Bright field photographic results indicated that poly-arginine (FIG. 6A) generated uncharacterized aggregates that were not seen in the control (FIG. 6B). FIG. 6C and FIG. 6D show fluorescently photographic results which indicated that poly-arginine enhanced the uptake of fluorescein-dextran as indicated by higher green fluorescence found in the poly-arginine treated eggs (FIG. 6C) than that of control eggs (FIG. 6D).

Example 4

A dendrimeric octaguanidine with a triazine core also known as Vivo, was conjugated to zebrafish dnd-MO, and used in an immersion containing zebrafish embryos in water. The ability of methods disclosed herein to induce sterility in zebrafish was tested by administering the following:

A: dnd-MO-Vivo 60 µM for 0.5 hour, 40 µM for 2 hours, 20 µM for 3 hours, 10 µM for 4.5 hours and 5 µM for 14 hours, administration began at the start of water activation and water hardening (immediately after fertilization);

B: water-only solution as control;

C: dnd-MO-Vivo 60 µM for 0.5 hour, 40 µM for 2 hours, 20 µM for 3 hours, 10 µM for 4.5 hours and 5 µM for 14 hours, administration began at one hour post-fertilization.

In zebrafish, 100% sterility induction can be achieved only when dnd-MO-Vivo was administered immediately starting at water activation and water hardening. If dnd-MO-Vivo was administered 1 hour after water activation only 44-59% treated fish were infertile (Table 1).

TABLE 1

|  | A1 | A2 | B1 | B2 | C1 | C2 |
|---|---|---|---|---|---|---|
| embryos survived to 2 dpf (days post-fertilization) | 41 | 40 | 52 | 50 | 45 | 47 |
| adult fish obtained | 28 | 32 | 39 | 43 | 34 | 29 |
| adult survival rate | 50% | 57% | 69% | 76% | 60% | 51% |
| number of males | 0 | 0 | 16 | 15 | 12 | 9 |
| number of females | 0 | 0 | 23 | 28 | 7 | 3 |
| number of infertile fish | 28 | 32 | 0 | 0 | 15 | 17 |
| % of infertile fish | 100% | 100% | 0% | 0% | 44% | 59% |
| Average % of infertile fish |  | 100% |  | 0% |  | 52% |

Example 5

A dendrimeric octaguanidine with a triazine core also known as Vivo, was conjugated to salmonids' dnd-MO, 5'-CTGACTTGAACGCTCCTCCATTATC-3' (SEQ ID NO. 3) and used in an immersion containing rainbow trout embryos in water, or unfertilized eggs in ovarian fluid or fertilization diluent. The ability of methods disclosed herein to induce sterility in rainbow trout was tested by administering the following:

I: Salmonids' dnd-MO-Vivo 10 µM for 48 hours, administration to fertilized eggs at the beginning of water activation (within 1 minute)

II: Salmonids' dnd-MO-Vivo 10 µM for 48 hours, administration to unfertilized eggs with the immersion medium of the ovarian fluid. The fertilization was conducted after 48 hours of incubation.

III: Salmonids' dnd-MO-Vivo 10 µM for 48 hours, administration to unfertilized eggs with the fertilization diluent that contains salt, Tris (pH 8.0), Glycine, and 5% of fish serum. The fertilization was conducted after 48 hours of incubation.

IV: Water or immersion medium only without salmonids' dnd-MO-Vivo as controls.

FIG. 7A-7G shows that salmonids' dnd-MO-Vivo treatment induced infertility in rainbow trout. (FIG. 7A) a well-developed testis of untreated control male fish from treatment IV; (FIG. 7B) a well-developed ovary of untreated control female fish from treatment IV; (FIG. 7C) the gonads of salmonids' 10 μM dnd-MO-Vivo treated fish in treatments I, II and III, developed into a thin filament-like tissue; (FIG. 7D) a photomicrograph of dissected gonads; (FIG. 7E) the active spermatogenesis of the testis of an untreated control (treatment IV) male fish; (FIG. 7F) a well-developed ovary of an untreated control female (treatment IV) with oocytes at different developmental stages; (FIG. 7G) the histological examinations of gonadal tissue show the gonad of a salmonids' dnd-MO-Vivo treated fish (treatment I, II and III) that appears to be under-developed without advanced gonadal structure or germ cells.

Example 6

A salmonids' dnd-MO (see Example 5) or a dendrimeric octaguanidine with a triazine core also known as Vivo, which was conjugated to salmonids' dnd-MO, resulting in salmonids' dnd-MO-Vivo, was used to induce sterility in Atlantic salmon and was tested by administering the following:

I: Salmonids' dnd-MO-Vivo 10 μM for 48 hours, administration to fertilized eggs at the beginning of water activation (within 1 minute).
II: Salmonids' dnd-MO-Vivo 10 μM for 48 hours, administration to unfertilized eggs with the immersion medium of the ovarian fluid. The eggs were fertilized after 48 hours of incubation.
III: Salmonids' dnd-MO-Vivo 10 μM for 48 hours, administration to unfertilized eggs with the immersion medium that contains salt, Tris (pH 8.0), Glycine, and 5% of fish serum. The fertilization was conducted after 48 hours of incubation.
IV: Salmonids' dnd-MO 20 μM for 48 hours, administration to unfertilized eggs with the immersion medium of the ovarian fluid. The eggs were fertilized after 48 hours of incubation.
V: Salmonids' dnd-MO 20 μM for 48 hours, administration to unfertilized eggs with the immersion medium that contains salt, Tris (pH 8.0), Glycine, and 5% of fish serum. The eggs were fertilized after 48 hours of incubation.
VI: Water or immersion medium only without neither salmonids' dnd-MO-Vivo nor dnd-MO as controls.

Figures 8A, 8B, 8C, 8D:
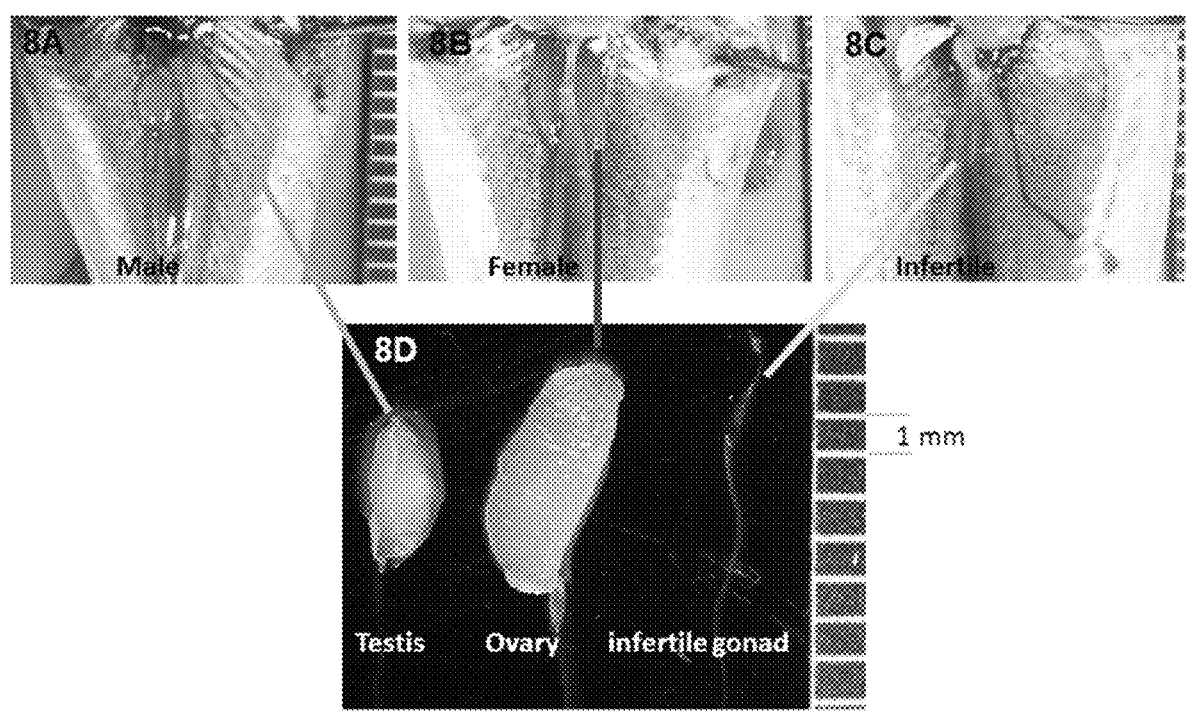
FIG. 8A-8D are photomicrographs showing that salmonids' dnd-MO or dnd-MO-Vivo treatment blocked gonadal development in Atlantic salmon. In 10-month-old Atlantic salmon, (FIG. 8A) a developing testis of untreated male.

FIG. 8A-8D shows that salmonids' dnd-MO or dnd-MO-Vivo treatment blocked gonadal development in Atlantic salmon. In 10-month-old Atlantic salmon, (FIG. 8A) A developing testis of untreated (treatment VI) male; (FIG. 8B) a developing ovary of untreated (treatment VI) female; (FIG. 8C) the gonads of dnd-MO-Vivo treated (treatments I, II, III) or dnd-MO treated (treatments IV, V) fish developed into a thin filament-like tissue; (FIG. 8D) a photomicrograph of dissected gonads from (FIG. 8A), (FIG. 8B) and (FIG. 8C).

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

INDUSTRIAL APPLICABILITY

The disclosure provides methods for delivering agents to eggs/embryos of aquatic animals using guanidine-containing compounds to enhance the permeability of the chorion of the eggs. Delivery of drug candidates or potentially bioactive agents to the eggs/embryos of aquatic animals, such as zebrafish, offer opportunities for screening and evaluation of the activity and/or toxicity of such test agents.

The methods and compounds of the disclosure further produce reproductively sterile fish and aquatic egg-producing animals. Sterilization (induced infertility) of farmed fish and aquatic egg-producing animals enhances their growth rate by increasing the conversion of food energy to muscle growth, instead of gonadal development. In addition, if escaped from aquaculture operations to the environment, reproductively sterile farmed fish and egg-producing aquatic animals, including domesticated, non-native or genetically modified species, will not be able to reproduce or inter-breed with wild stock. This will assist biological containment and prevent genetic contamination of wild populations and/or the establishment in the wild of domestic, non-native or genetically modified farmed fish and aquatic egg-producing animals.

What is claimed is:

1. A method of delivering at least one agent into egg(s) from an egg-producing aquatic animal, said method comprising contacting the egg(s) with the at least one agent in the presence of a guanidine-containing compound that is effective to enhance permeability of the chorion of the egg(s), wherein the egg(s) are contacted with the at least one agent in an immersion medium comprising the at least one agent and the guanidine-containing compound and wherein the guanidine-containing compound (a) comprises arginine or a salt thereof; or (b) is guanidine or a salt thereof selected from the group consisting of guanidine-HCl, guanidine-thiocyanate, guanidine-acetate, guanidine-carbonate, guanidine-nitrate, guanidine-sulfate, guanidine-bicarbonate, and guanidine-hydrobromide; or (c) comprises a dimer, trimer or polymer of guanidine or arginine selected from the compounds of general formulas (I) to (IV), wherein the compound of general formula (I) is selected from an arginine dimer and contiguous poly-arginine, of the formula:

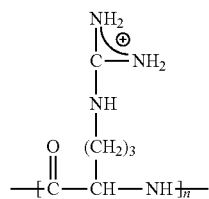

(I)

wherein: n≥2;

wherein the compound of general formula (II) is selected from an arginine-linker compound dimer and spaced poly-arginine-linker compound, of the formula:

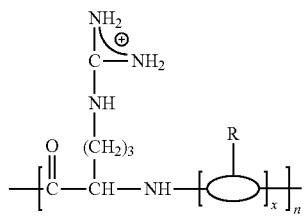

(II)

wherein: n≥2;

○ is a variable backbone linker and is an amino acid, nucleotide, phosphoramidate, glycol, polyethylene glycol, nitro, amino, cyano, phenyl, cyclohexyl, benzyl, or a linear or branched $C_1$-$C_4$ lower alkyl;

X≥2; and

R is a variable group and is a hydrogen atom, nitro, amino, cyano, phenyl, cyclohexyl, benzyl, or a linear or branched $C_1$-$C_4$ lower alkyl or $C_1$-$C_4$ alkenyl radical, optionally substituted with one or two radicals chosen from: hydroxyl, amino, dimethylamino, methoxy, ethoxy, carboxyl, carboxamide, N-methylcarboxamide or $SO_3H$, or salts thereof;

wherein the compound of general formula (III) is selected from a guanidine-linker compound dimer and contiguous poly-guanidine-linker compound, of the formula:

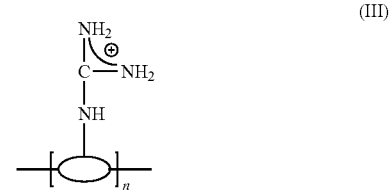

(III)

wherein: n≥2; and

○ is a variable backbone linker and is an amino acid, nucleotide, phosphoramidate, glycol, polyethylene glycol, nitro, amino, cyano, phenyl, cyclohexyl, benzyl, or a linear or branched $C_1$-$C_4$ lower alkyl; and wherein the compound of general formula (IV) is selected from a guanidine-linker compound dimer and spaced poly-guanidine-linker compound, of the formula:

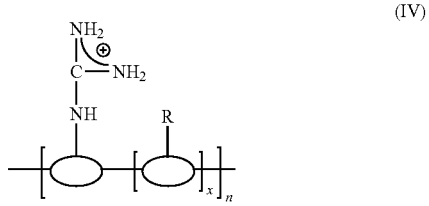

(IV)

wherein: n≥2;

○ is a variable backbone linker and is an amino acid, nucleotide, phosphoramidate, glycol, polyethylene glycol, nitro, amino, cyano, phenyl, cyclohexyl, benzyl, or a linear or branched $C_1$-$C_4$ lower alkyl;

X≥2; and

R is a variable group and is a hydrogen atom, nitro, amino, cyano, phenyl, cyclohexyl, benzyl, or a linear or branched $C_1$-$C_4$ lower alkyl or $C_1$-$C_4$ alkenyl radical, optionally substituted with one or two radicals chosen from: hydroxyl, amino, dimethylamino, methoxy, ethoxy, carboxyl, carboxamide, N-methylcarboxamide or $SO_3H$, or salts thereof.

2. The method of claim 1, wherein concentration of the guanidine-containing compound in the immersion medium is in a range of from 1 to 80,000 μM.

3. The method of claim 1, wherein the guanidine-containing compound comprises arginine or a salt thereof.

4. The method of claim 1 wherein the guanidine-containing compound is arginine.

5. The method of claim 1, wherein the guanidine-containing compound is guanidine.

6. The method of claim 1, wherein the guanidine-containing compound is guanidine-HCl, guanidine-thiocyanate, guanidine-acetate, guanidine-carbonate, guanidine-nitrate, guanidine-sulfate, guanidine-bicarbonate, or guanidine-hydrobromide.

7. The method of claim 1, wherein the guanidine-containing compound comprises a dimer, trimer or polymer of guanidine or arginine selected from the compounds of general formulas (I) to (IV), wherein the compound of general formula (I) is selected from an arginine dimer and contiguous poly-arginine, of the formula:

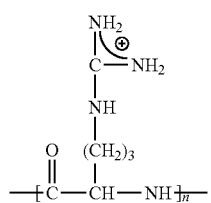

(I)

wherein: n≥2;

wherein the compound of general formula (II) is selected from an arginine-linker compound dimer and spaced poly-arginine-linker compound, of the formula:

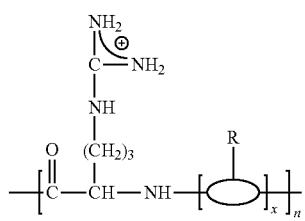

(II)

wherein: n≥2;

○ is a variable backbone linker and is an amino acid, nucleotide, phosphoramidate, glycol, polyethylene glycol, nitro, amino, cyano, phenyl, cyclohexyl, benzyl, or a linear or branched $C_1$-$C_4$ lower alkyl;

X≥2; and

R is a variable group and is a hydrogen atom, nitro, amino, cyano, phenyl, cyclohexyl, benzyl, or a linear or branched $C_1$-$C_4$ lower alkyl or $C_1$-$C_4$ alkenyl radical, optionally substituted with one or two radicals chosen from: hydroxyl, amino, dimethylamino, methoxy, ethoxy, carboxyl, carboxamide, N-methylcarboxamide or $SO_3H$, or salts thereof;

wherein the compound of general formula (III) is selected from a guanidine-linker compound dimer and contiguous poly-guanidine-linker compound, of the formula:

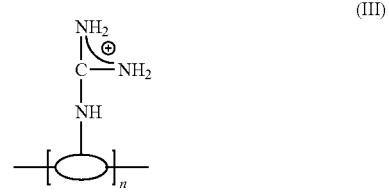

(III)

wherein: n≥2; and

○ is a variable backbone linker and is an amino acid, nucleotide, phosphoramidate, glycol, polyethylene glycol, nitro, amino, cyano, phenyl, cyclohexyl, benzyl, or a linear or branched $C_1$-$C_4$ lower alkyl; and wherein the compound of general formula (IV) is selected from a guanidine-linker compound dimer and spaced poly-guanidine-linker compound, of the formula:

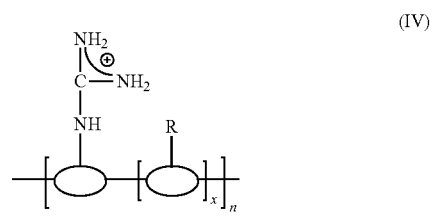

(IV)

wherein: n≥2;

○ is a variable backbone linker and is an amino acid, nucleotide, phosphoramidate, glycol, polyethylene glycol, nitro, amino, cyano, phenyl, cyclohexyl, benzyl, or a linear or branched $C_1$-$C_4$ lower alkyl;

X≥2; and

R is a variable group and is a hydrogen atom, nitro, amino, cyano, phenyl, cyclohexyl, benzyl, or a linear or branched $C_1$-$C_4$ lower alkyl or $C_1$-$C_4$ alkenyl radical, optionally substituted with one or two radicals chosen from: hydroxyl, amino, dimethylamino, methoxy, ethoxy, carboxyl, carboxamide, N-methylcarboxamide or $SO_3H$, or salts thereof.

8. The method of claim 1, wherein the guanidine-containing compound is poly-arginine/9 mer.

9. The method of claim 1, wherein the at least one agent is selected from the group consisting of antibodies, proteins, peptides, RNAs, and DNAs.

10. The method of claim 1, wherein the at least one agent is an anti-sense Morpholino oligomer that is effective to suppress expression of a gene essential for gonadal development in the egg-producing aquatic animal.

11. The method of claim 10, wherein the anti-sense Morpholino oligomer suppresses expression of the dead end, nanos, vasa, gnrh or fsh receptor gene in the egg-producing aquatic animal.

12. The method of claim 11, wherein the anti-sense Morpholino oligomer suppresses expression of the dead end gene in the egg-producing aquatic animal.

13. The method of claim 1 for producing reproductively sterile egg-producing aquatic animals, wherein the agent is an anti-sense Morpholino oligomer that is effective to transfect the egg(s) and render individual(s) produced therefrom reproductively sterile.

14. The method of claim 13, wherein the egg(s) are fertilized or unfertilized egg(s) of a fish selected from the group consisting of salmonids, moronids, and cichlids.

15. The method of claim 13, wherein said egg(s) are fertilized eggs and said method comprising contacting said fertilized egg(s) immediately after fertilization and including the period of water activation and water hardening with anti-sense Morpholino oligomer that is effective to transfect the egg(s) and render individual(s) produced therefrom reproductively sterile.

16. The method of claim 13, wherein the anti-sense Morpholino oligomer is the oligomer with the nucleotide sequence of SEQ ID NO: 1 or SEQ ID NO: 2 or a variant thereof.

17. The method of claim 16, wherein the egg(s) are fertilized or unfertilized egg(s) of a fish selected from the group consisting of salmonids, moronids, and cichlids.

18. The method of claim 17, wherein the egg(s) are fertilized egg(s), said method comprising contacting said fertilized egg(s) immediately after fertilization and including the period of water activation and water hardening with anti-sense Morpholino oligomer that is effective to transfect the egg(s) and render individual(s) produced therefrom reproductively sterile.

19. The method of claim 1, wherein the guanidine-containing compound is covalently bound to the agent.

20. A transfected egg of an egg-producing aquatic animal obtained by a method according to claim 1, said egg comprising a chorion-permeated amount of said at least one agent and a chorion-permeated amount of said guanidine-containing compound.

21. The transfected egg of claim 20, wherein said at least one agent comprises an anti-sense Morpholino oligomer that is effective to suppress expression of a gene essential for gonadal development in the egg-producing aquatic animal.

22. The transfected egg of claim 21 wherein the anti-sense Morpholino oligomer suppresses expression of the dead end, nanos, vasa, gnrh orfsh receptor gene in the egg-producing aquatic animal.

23. The transfected egg of claim 22, wherein the anti-sense Morpholino oligomer suppresses expression of the dead end gene in the egg-producing aquatic animal.

24. The transfected egg of claim 23, wherein the anti-sense Morpholino oligomer is the oligomer with the nucleotide sequence of SEQ ID NO: 1 or SEQ ID NO: 2 or a variant thereof.

25. The transfected egg of claim 21, wherein the anti-sense Morpholino oligomer renders an individual produced from such egg reproductively sterile.

26. The transfected egg of claim 23, wherein the guanidine-containing compound is poly-arginine/9 mer.

27. The transfected egg of claim 20, wherein the guanidine-containing compound is covalently bound to the at least one agent.

28. The transfected egg of claim 27 wherein said at least one agent comprises an anti-sense Morpholino oligomer that is effective to suppress expression of a gene essential for gonadal development in the egg-producing aquatic animal.

29. The transfected egg of claim 28, wherein the anti-sense Morpholino oligomer suppresses expression of the dead end, nanos, vasa, gnrh or fsh receptor gene in the egg-producing aquatic animal.

30. The transfected egg of claim 29, wherein the anti-sense Morpholino oligomer suppresses expression of the dead end gene in the egg-producing aquatic animal.

31. The transfected egg of claim 30, wherein the anti-sense Morpholino oligomer is the oligomer with the nucleotide sequence of SEQ ID NO: 1 or SEQ ID NO: 2 or a variant thereof.

32. The transfected egg of claim 30, wherein the guanidine-containing compound is poly-arginine/9 mer.

33. The transfected egg of claim 27, wherein the anti-sense Morpholino oligomer renders an individual produced from such egg reproductively sterile.

* * * * *